(12) United States Patent
Jäkel et al.

(10) Patent No.: US 8,697,713 B2
(45) Date of Patent: Apr. 15, 2014

(54) PYRROLOPYRIMIDINES FOR PHARMACEUTICAL COMPOSITIONS

(75) Inventors: Stefan Jäkel, Darmstadt (DE); Tanja Reuter, Darmstadt (DE); Stephen Murfin, Didcot (GB); Thomas Stephen Coulter, Wantage (GB); Steven Taylor, Didcot (GB)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 555 days.

(21) Appl. No.: 12/373,224

(22) PCT Filed: Jul. 10, 2007

(86) PCT No.: PCT/EP2007/006109
§ 371 (c)(1),
(2), (4) Date: Dec. 16, 2009

(87) PCT Pub. No.: WO2008/006547
PCT Pub. Date: Jan. 17, 2008

(65) Prior Publication Data
US 2010/0105708 A1    Apr. 29, 2010

(30) Foreign Application Priority Data
Jul. 10, 2006  (EP) ..................................... 06014297

(51) Int. Cl.
*A01N 43/90* (2006.01)
*A61K 31/519* (2006.01)
*C07D 487/00* (2006.01)

(52) U.S. Cl.
USPC ........................ 514/265.1; 544/280

(58) Field of Classification Search
None
See application file for complete search history.

(56) References Cited

U.S. PATENT DOCUMENTS

| | | |
|---|---|---|
| 5,686,457 A | 11/1997 | Traxler et al. |
| 6,096,749 A | 8/2000 | Traxler et al. |
| 6,395,733 B1 | 5/2002 | Arnold et al. |
| 6,784,174 B1 | 8/2004 | Cumming |
| 2001/0027197 A1 | 10/2001 | Bridges et al. |
| 2003/0162795 A1 | 8/2003 | Munchhof et al. |
| 2006/0020042 A1 | 1/2006 | McDonald et al. |
| 2007/0099877 A1 | 5/2007 | Cai et al. |
| 2010/0015708 A1 | 1/2010 | Quay et al. |
| 2010/0056548 A1 | 3/2010 | Aicher et al. |
| 2010/0143341 A1 | 6/2010 | Taylor et al. |
| 2010/0247517 A1 | 9/2010 | Austen et al. |
| 2011/0021203 A1 | 1/2011 | Yamada et al. |
| 2011/0212102 A1 | 9/2011 | Lehmann-Lintz et al. |
| 2011/0217311 A1 | 9/2011 | Lehmann-Lintz et al. |
| 2012/0128686 A1 | 5/2012 | Austen et al. |
| 2013/0056914 A1 | 3/2013 | Frankowski et al. |

FOREIGN PATENT DOCUMENTS

| | | | |
|---|---|---|---|
| CA | 2038521 A1 | 9/1991 | |
| CH | 408945 A | 3/1966 | |
| DE | 3036390 A1 | 5/1982 | |
| DE | 248593 A1 | 8/1987 | |
| EP | 0447891 A1 | 9/1991 | |
| EP | 0452002 A2 | 10/1991 | |
| EP | 682027 * | 4/1995 | ........... C07D 487/04 |
| EP | 0682027 A1 | 11/1995 | |
| EP | 0729758 A2 | 9/1996 | |
| EP | 1724268 A1 | 11/2006 | |
| JP | 2005503345 A | 2/2005 | |
| WO | 9413677 A1 | 6/1994 | |
| WO | 9713771 A1 | 4/1997 | |
| WO | 9924440 A1 | 5/1999 | |
| WO | WO00/56738 A | 9/2000 | |
| WO | 2007075145 A1 | 12/2000 | |
| WO | 02088138 A1 | 11/2002 | |
| WO | 03037362 A2 | 5/2003 | |
| WO | 2004037159 A2 | 5/2004 | |
| WO | 2004106340 A2 | 12/2004 | |
| WO | 2004113347 A1 | 12/2004 | |
| WO | 2005010008 A1 | 2/2005 | |
| WO | 2005042537 A1 | 5/2005 | |

(Continued)

OTHER PUBLICATIONS

West, et. al., Journal of Organic Chemistry (1961), 26, 3809-12.*
Iwamura, et. al., Journal of Medicinal Chemistry (1983), 26(6), 838-44.*

(Continued)

*Primary Examiner* — Jeffrey H Murray
(74) *Attorney, Agent, or Firm* — Michael P. Morris; Edward S. Lazer

(57) ABSTRACT

The present invention relates to novel pyrrolopyrimidine compounds of the general formula (1) and pharmaceutical compositions comprising said pyrrolopyrimidine compounds. Moreover, the present invention relates to the use of the pyrrolopyrimidine compounds of the invention for the production of pharmaceutical compositions for the prophylaxis and/or treatment of diseases which can be influenced by the inhibition of the kinase activity of Mnk1 and/or Mnk2 (Mnk2a or Mnk2b) and/or variants thereof.

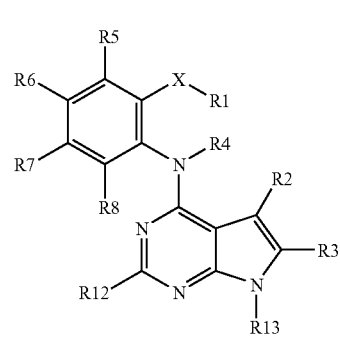

(I)

16 Claims, No Drawings

(56) References Cited

FOREIGN PATENT DOCUMENTS

| | | | |
|---|---|---|---|
| WO | 2005067546 A2 | 7/2005 | |
| WO | 2005080377 A1 | 9/2005 | |
| WO | 2005117890 A2 | 12/2005 | |
| WO | 2006014325 A2 | 2/2006 | |
| WO | WO2006/066937 A2 | 6/2006 | |
| WO | 2006094791 A1 | 9/2006 | |
| WO | 2006124874 A2 | 11/2006 | |
| WO | 2006136402 A1 | 12/2006 | |
| WO | 2007056214 A2 | 5/2007 | |
| WO | 2007056215 A2 | 5/2007 | |
| WO | 2007059905 A2 | 5/2007 | |
| WO | 2007081517 A2 | 7/2007 | |
| WO | 2007084815 A2 | 7/2007 | |
| WO | 2007115822 A2 | 7/2007 | |
| WO | 2007147874 A1 | 12/2007 | |
| WO | 2008006547 A2 | 1/2008 | |
| WO | 2008041053 A2 | 4/2008 | |
| WO | 2009065596 A2 | 5/2009 | |
| WO | 2010023181 A1 | 3/2010 | |
| WO | 2011104334 A1 | 9/2011 | |
| WO | 2011104337 A1 | 9/2011 | |
| WO | 2011104338 A1 | 9/2011 | |
| WO | 2011104340 A1 | 9/2011 | |

OTHER PUBLICATIONS

Traxler, et al, "4-(Phenylamino)Pyrrolopyrimidines: Potent and Selective, ATP Site Directed Inhibitors of the EGF-Receptor Protein Tyrosine Kinase", Journal of Medicinal Chemistry, American Chemical Society, Dec. 1996, pp. 2285-2292, Washington, US.

Jorgensen, et al, "Phosphorous Pentoxide in Organic Synthesis. XX 1. Synthesis of N-Aryl-7H-Pyrollo 2,3-Dpyrimidin-4-Amines", Journal of Heterocyclic Chemistry, Heterocorporation, May 1, 1985, pp. 859-863, Provo, US.

Traxler et al, "Use of a Pharmacophore Model for the Design of EGF-R Tyrosine Kinase Inhibitors: 4-(Phenylamino)Pyrazolo3,4-Dpyrimidines", Journal of Medicinal Chemistry, American Chemical Society, vol. 40, No. 22, 1997, pp. 3601-3616, Washington, US.

Banker, Gilbert S., et al; Modern Pharmaceutics (1996) 3rd Ed. Marcel Dekker, Inc. New York, p. 596.

Cheng, C.C., et al; Potential Purine Antagonists. VI. Synthesis of 1-Alkyl-and 1-Aryl-4-substituted Pyrazolo[3,4-d] pyrimidines1,2; Journal of Organic Chemistry, American Chemical Society (1956) vol. 21 pp. 1240-1256.

Dörwald, Florencio Zaragoza, et al; Side Reactions in Organic Synthesis: A Guide to Successful Synthesys Design; (2005) Wiley; VCH, Weinheim p. IX of preface.

http://www.medterms.com/script/main/art.asp?articlekey=12063, last accessed on Aug. 24, 2010.

International Search Report for PCT/EP2006/005980 mailed Nov. 16, 2006.

International Search Report for PCT/EP2007/003186 mailed Jun. 8, 2007.

International Search Report for PCT/EP2007/006109 mailed Dec. 20, 2007.

International Search Report for PCT/EP2009/060876 mailed Nov. 10, 2009.

International Search Report for PCT/EP2011/052810 mailed May 16, 2011.

International Search Report for PCT/EP2011/052811/mailed May 18, 2011.

International Search Report for PCT/EP2011/052813 mailed May 30, 2011.

International Search Reportfor PCT/EP2008/009880 mailed Jun. 25, 2009.

Mogensen, Jorgen, et al; Phosphorus Pentoxide in Organic Synthesis: XXXIV. Synthesis of 3-Arylthieno[2,3-d] pyrimidin-4(3H)-imines and their Rearrangement to N-arylthieno[2,3-d]pyrimidin-4-amines; Chemica Scripta (1988) vol. 28 pp. 195-200.

Munchhof, Michael J., et al; Design and SAR of Thienopyrimidine and Thienopyridine Inhibitors of VEGFR-2 Kinase Activity; Bioorganic & Medicinal Chemistry Letters (2004) vol. 14 pp. 21-24.

Peat, Andrew, J., et al; Novel Pyrazolopyrimidine Derivates as GSK-3 Inhibitors; Bioorganic & Medicinal Chemistry Letters (2004) vol. 14 pp. 2121-2125.

Showalter, H. D. Hollis, et al; Tyrosine Kinase Inhibitors. 16. 6,5,6-Tricyclic Benzothieno[3-,2-d]pyrimidines and Pyrimido[5,4-b]- and -[4,5-b]indoles as Potent Inhibitors of the Epidermal Growth Factor Receptor Tyrosine Kinase; Journal of Medicinal Chemistry (1999) vol. 42 pp. 5464-5474.

Sobolov, Susan B., et al; Selective N-Alkylation of Pyrrolopyrimidines and Indoles by "Transfer of Activation"; Tetrahedron Letters (1998) vol. 39 pp. 5685-5688.

Wolff, Manfred, E.; Principles and Practice; Burger's Medicinal Chemistry and Drug Discovery (1995) 5ed, vol. 1 pp. 975-977.

Young, Rodney, C., et al; Purine Derivates as Competitive Inhibitors of Human Erythrocyte Membrane Phosphatidylinositol 4-Kinase; Journal of Medicinal Chemistry (1990) vol. 33 pp. 2073-2080.

* cited by examiner

SEQUENCE LISTING

```
<160> NUMBER OF SEQ ID NOS: 10

<210> SEQ ID NO 1
<211> LENGTH: 29
<212> TYPE: DNA
<213> ORGANISM: Homo sapiens

<400> SEQUENCE: 1
tttaggatcc gtatcttctc aaaagttgg                                    29

<210> SEQ ID NO 2
<211> LENGTH: 28
<212> TYPE: DNA
<213> ORGANISM: Homo sapiens

<400> SEQUENCE: 2
ctgggtcgac tcagagtgct gtgggcgg                                     28

<210> SEQ ID NO 3
<211> LENGTH: 28
<212> TYPE: DNA
<213> ORGANISM: Homo sapiens

<400> SEQUENCE: 3
acagggatcc gtgcagaaga aaccagcc                                     28

<210> SEQ ID NO 4
<211> LENGTH: 29
<212> TYPE: DNA
<213> ORGANISM: Homo sapiens

<400> SEQUENCE: 4
gatggtcgac tcaggcgtgg tctcccacc                                    29

<210> SEQ ID NO 5
<211> LENGTH: 12
<212> TYPE: PRT
<213> ORGANISM: Homo sapiens
```

```
<400> SEQUENCE: 5

Thr Ala Thr Lys Ser Gly Ser Thr Thr Lys Asn Arg
1               5                   10

<210> SEQ ID NO 6
<211> LENGTH: 31
<212> TYPE: DNA
<213> ORGANISM: Homo sapiens

<400> SEQUENCE: 6
agccgtcgac gcggcggcgg cggcggcggg c                              31

<210> SEQ ID NO 7
<211> LENGTH: 30
<212> TYPE: DNA
<213> ORGANISM: Homo sapiens

<400> SEQUENCE: 7
tgacaagctt aagatctgta tcctggctgg                                30

<210> SEQ ID NO 8
<211> LENGTH: 31
<212> TYPE: DNA
<213> ORGANISM: Homo sapiens

<400> SEQUENCE: 8
gtccggatcc cccaagaaga agccgacgcc c                              31

<210> SEQ ID NO 9
<211> LENGTH: 30
<212> TYPE: DNA
<213> ORGANISM: Homo sapiens

<400> SEQUENCE: 9
tcccgtcgac ttagacgcca gcagcatggg                                30

<210> SEQ ID NO 10
<211> LENGTH: 17
<212> TYPE: PRT
<213> ORGANISM: Homo sapiens

<400> SEQUENCE: 10

Phe Phe Lys Asn Ile Val Thr Pro Arg Thr Pro Pro Ser Gln Gly
1               5                   10                  15
Lys
```

PYRROLOPYRIMIDINES FOR PHARMACEUTICAL COMPOSITIONS

The present invention relates to pyrrolopyrimidine compounds and to novel pharmaceutical compositions comprising pyrrolopyrimidine compounds.

Moreover, the present invention relates to the use of the pyrrolopyrimidine compounds of the invention for the production of pharmaceutical compositions for the prophylaxis and/or treatment of diseases which can be influenced by the inhibition of the kinase activity of Mnk1 (Mnk1a or MnK1b) and/or Mnk2 (Mnk2a or Mnk2b) or further variants thereof. Particularly, the present invention relates to the use of the pyrrolopyrimidine compounds of the invention for the production of pharmaceutical compositions for the prophylaxis and/or therapy of metabolic diseases, such as diabetes, hyperlipidemia and obesity, hematopoietic disorders and cancer and their consecutive complications and disorders associated therewith as well as inflammations.

Metabolic diseases are diseases caused by an abnormal metabolic process and may either be congenital due to an inherited enzyme abnormality or acquired due to a disease of an endocrine organ or failure of a metabolically important organ such as the liver or the pancreas.

The present invention is more particularly directed to the treatment and/or prophylaxis of in particular metabolic diseases of the lipid and carbohydrate metabolism and the consecutive complications and disorders associated therewith.

Lipid disorders cover a group of conditions which cause abnormalities in the level and metabolism of plasma lipids and lipoproteins. Thus, hyperlipidemias are of particular clinical relevance since they constitute an important risk factor for the development of atherosclerosis and subsequent vascular diseases such as coronary heart disease.

Diabetes mellitus is defined as a chronic hyperglycemia associated with resulting damages to organs and dysfunctions of metabolic processes. Depending on its etiology, one differentiates between several forms of diabetes, which are either due to an absolute (lacking or decreased insulin secretion) or to a relative lack of insulin. Diabetes mellitus Type I (IDDM, insulin-dependent diabetes mellitus) generally occurs in adolescents under 20 years of age. It is assumed to be of auto-immune etiology, leading to an insulitis with the subsequent destruction of the beta cells of the islets of Langerhans which are responsible for the insulin synthesis. In addition, in latent autoimmune diabetes in adults (LADA; Diabetes Care. 8: 1460-1467, 2001) beta cells are being destroyed due to autoimmune attack. The amount of insulin produced by the remaining pancreatic islet cells is too low, resulting in elevated blood glucose levels (hyperglycemia). Diabetes mellitus Type II generally occurs at an older age. It is above all associated with a resistance to insulin in the liver and the skeletal muscles, but also with a defect of the islets of Langerhans. High blood glucose levels (and also high blood lipid levels) in turn lead to an impairment of beta cell function and to an increase in beta cell apoptosis.

Diabetes is a very disabling disease, because today's common anti-diabetic drugs do not control blood sugar levels well enough to completely prevent the occurrence of high and low blood sugar levels. Out of range blood sugar levels are toxic and cause long-term complications for example retinopathy, renopathy, neuropathy and peripheral vascular disease. There is also a host of related conditions, such as obesity, hypertension, heart disease and hyperlipidemia, for which persons with diabetes are substantially at risk.

Obesity is associated with an increased risk of follow-up diseases such as cardiovascular diseases, hypertension, diabetes, hyperlipidemia and an increased mortality. Diabetes (insulin resistance) and obesity are part of the "metabolic syndrome" which is defined as the linkage between several diseases (also referred to as syndrome X, insulin-resistance syndrome, or deadly quartet). These often occur in the same patients and are major risk factors for development of diabetes type II and cardiovascular disease. It has been suggested that the control of lipid levels and glucose levels is required to treat diabetes type II, heart disease, and other occurrences of metabolic syndrome (see e.g., Diabetes 48: 1836-1841, 1999; JAMA 288: 2209-2716, 2002).

In one embodiment of the present invention the compounds and compositions of the present invention are useful for the treatment and/or prophylaxis of metabolic diseases of the carbohydrate metabolism and their consecutive complications and disorders such as impaired glucose tolerance, diabetes (preferably diabetes type II), diabetic complications such as diabetic gangrene, diabetic arthropathy, diabetic osteopenia, diabetic glomerosclerosis, diabetic nephropathy, diabetic dermopathy, diabetic neuropathy, diabetic cataract and diabetic retinopathy, diabetic maculopathy, diabetic feet syndrome, diabetic coma with or without ketoacidosis, diabetic hyperosmolar coma, hypoglycemic coma, hyperglycemic coma, diabetic acidosis, diabetic ketoacidosis, intracapillary glomerulonephrosis, Kimmelstiel-Wilson syndrome, diabetic amyotrophy, diabetic autonomic neuropathy, diabetic mononeuropathy, diabetic polyneuropathy, diabetic angiopathies, diabetic peripheral angiopathy, diabetic ulcer, diabetic arthropathy, or obesity in diabetes.

In a further embodiment the compounds and compositions of the present invention are useful for the treatment and/or prophylaxis of metabolic diseases of the lipid metabolism (i.e. lipid disorders) and their consecutive complications and disorders such as hypercholesterolemia, familial hypercholesterolemia, Fredrickson's hyperlipoproteinemia, hyperbetalipoproteinemia, hyperlipidemia, low-density-lipoprotein-type [LDL] hyperlipoproteinemia, pure hyperglyceridemia, endogenous hyperglyceridemia, isolated hypercholesterolemia, isolated hypertroglyceridemia, cardiovascular diseases such as hypertension, ischemia, varicose veins, retinal vein occlusion, atherosclerosis, angina pectoris, myocardial infarction, stenocardia, pulmonary hypertension, congestive heart failure, glomerulopaty, tubulointestitial disorders, renal failure, angiostenosis, or cerebrovascular disorders, such as cerebral apoplexy.

In a further embodiment of the present invention the compounds and compositions of the present invention are useful for the treatment and/or prophylaxis of hematopoetic disorders and their consecutive complications and disorders such as acute myeloid leukemia (AML), Morbus Hodgkin, Non-Hodgkin's lymphoma; hematopoetic disease, acute non-lymphocytic leukemia (ANLL), myeloproliferative disease acute promyelocytic leukemia (APL), acute myelomonocytic leukemia (AMMoL), polycythemia vera, lymphoma, acute lymphocytic leukemia (ALL), chronic lymphocytic leukemia (CCL), Wilm's tumor, or Ewing's Sarcoma.

In accordance with the invention the compounds and compositions of the present invention are useful in hematopoetic stem cell therapy.

In a further embodiment of the present invention the compounds and compositions of the present invention are useful for the treatment and/or prophylaxis of cancer and consecutive complications and disorders such as cancer of the upper gastrointestinal tract, pancreatic carcinoma, breast cancer, colon cancer, ovarian carcinoma, cervix carcinoma, corpus carcinoma, brain tumor, testicular cancer, laryngeal carcinoma, osteocarcinoma, prostatic cancer, retinoblastoma, liver carcinoma, lung cancer, neuroblastoma, renal carcinoma, thyroid carcinoma, esophageal cancer, soft tissue sarcoma, cachexia, or pain.

Furthermore, the present invention relates to the use of pyrrolopyrimidine compounds for the production of pharmaceutical compositions for the prophylaxis and/or therapy of cytokine related diseases.

Such diseases are i.a. inflammatory diseases, autoimmune diseases, destructive bone disorders, proliferative disorders, infectious diseases, neurodegenerative diseases, allergies, or other conditions associated with proinflammatory cytokines.

Allergic and inflammatory diseases such as acute or chronic inflammation, chronic inflammatory arthritis, rheumatoid arthritis, psoriasis, COPD, inflammatory bowel disease, asthma and septic shock and their consecutive complications and disorders associated therewith.

Inflammatory diseases like rheumatoid arthritis, inflammatory lung diseases like COPD, inflammatory bowel disease and psoriasis afflict one in three people in the course of their lives. Not only do those diseases impose immense health care costs, but also they are often crippling and debilitating.

Although inflammation is the unifying pathogenic process of these inflammatory diseases below, the current treatment approach is complex and is generally specific for any one disease. Many of the current therapies available today only treat the symptoms of the disease and not the underlying cause of inflammation.

The compositions of the present invention are useful for the treatment and/or prophylaxis of inflammatory diseases and consecutive complications and disorders. such as chronic or acute inflammation, inflammation of the joints such as chronic inflammatory arthritis, rheumatoid arthritis, psoriatic arthritis, osteoarthritis, juvenile rheumatoid arthritis, Reiter's syndrome, rheumatoid traumatic arthritis, rubella arthritis, acute synovitis and gouty arthritis; inflammatory skin diseases such as sunburn, psoriasis, erythrodermic psoriasis, pustular psoriasis, eczema, dermatitis, acute or chronic graft formation, atopic dermatitis, contact dermatitis, urticaria and scleroderma; inflammation of the gastrointestinal tract such as inflammatory bowel disease, Crohn's disease and related conditions, ulcerative colitis, colitis, and diverticulitis; nephritis, urethritis, salpingitis, oophoritis, endomyometritis, spondylitis, systemic lupus erythematosus and related disorders, multiple sclerosis, asthma, meningitis, myelitis, encephalomyelitis, encephalitis, phlebitis, thrombophlebitis, respiratory diseases such as asthma, bronchitis, chronic obstructive pulmonary disease (COPD), inflammatory lung disease and adult respiratory distress syndrome, and allergic rhinitis; endocarditis, osteomyelitis, rheumatic fever, rheumatic pericarditis, rheumatic endocarditis, rheumatic myocarditis, rheumatic mitral valve disease, rheumatic aortic valve disease, prostatitis, prostatocystitis, spondoarthropathies ankylosing spondylitis, synovitis, tenosynovotis, myositis, pharyngitis, polymyalgia rheumatica, shoulder tendonitis or bursitis, gout, pseudo gout, vasculitides, inflammatory diseases of the thyroid selected from granulomatous thyroiditis, lymphocytic thyroiditis, invasive fibrous thyroiditis, acute thyroiditis; Hashimoto's thyroiditis, Kawasaki's disease, Raynaud's phenomenon, Sjogren's syndrome, neuroinflammatory disease, sepsis, conjunctivitis, keratitis, iridocyclitis, optic neuritis, otitis, lymphoadenitis, nasopaharingitis, sinusitis, pharyngitis, tonsillitis, laryngitis, epiglottitis, bronchitis, pneumonitis, stomatitis, gingivitis. oesophagitis, gastritis, peritonitis, hepatitis, cholelithiasis, cholecystitis, glomerulonephritis, goodpasture's disease, crescentic glomerulonephritis, pancreatitis, endomyometritis, myometritis, metritis, cervicitis, endocervicitis, exocervicitis, parametritis, tuberculosis, vaginitis, vulvitis, silicosis, sarcoidosis, pneumoconiosis, pyresis, inflammatory polyarthropathies, psoriatric arthropathies, intestinal fibrosis, bronchiectasis and enteropathic arthropathies.

Moreover, cytokines are also believed to be implicated in the production and development of various cardiovascular and cerebrovascular disorders such as congestive heart disease, myocardial infarction, the formation of atherosclerotic plaques, hypertension, platelet aggregation, angina, stroke, Alzheimer's disease, reperfusion injury, vascular injury including restenosis and peripheral vascular disease, and, for example, various disorders of bone metabolism such as osteoporosis (including senile and postmenopausal osteoporosis), Paget's disease, bone metastases, hypercalcaemia, hyperparathyroidism, osteosclerosis, osteoporosis and periodontitis, and the abnormal changes in bone metabolism which may accompany rheumatoid arthritis and osteoarthritis.

Excessive cytokine production has also been implicated in mediating certain complications of bacterial, fungal and/or viral infections such as endotoxic shock, septic shock and toxic shock syndrome and in mediating certain complications of CNS surgery or injury such as neurotrauma and ischaemic stroke.

Excessive cytokine production has, moreover, been implicated in mediating or exacerbating the development of diseases involving cartilage or muscle resorption, pulmonary fibrosis, cirrhosis, renal fibrosis, the cachexia found in certain chronic diseases such as malignant disease and acquired immune deficiency syndrome (AIDS), tumour invasiveness and tumour metastasis and multiple sclerosis. The treatment and/or prophylaxis of these diseases are also contemplated by the present invention Additionally, the inventive compositions may be used to treat inflammation associated with autoimmune diseases including, but not limited to, systemic lupus erythematosis, Addison's disease, autoimmune polyglandular disease (also known as autoimmune polyglandular syndrome), glomerulonephritis, rheumatoid arthritis scleroderma, chronic thyroiditis, Graves' disease, autoimmune gastritis, diabetes, autoimmune hemolytic anemia, glomerulonephritis, rheumatoid arthritis autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, and graft vs. host disease.

In a further embodiment the compositions of the present invention may be used for the treatment and prevention of infectious diseases such as sepsis, septic shock, *Shigellosis*, and *Helicobacter pylori* and viral diseases including herpes simplex type 1 (HSV-1), herpes simplex type 2 (HSV-2), cytomegalovirus, Epstein-Barr, human immunodeficiency virus (HIV), acute hepatitis infection (including hepatitis A, hepatitis B, and hepatitis C), HIV infection and CMV retinitis, AIDS or malignancy, malaria, mycobacterial infection and meningitis. These also include viral infections, by influenza virus, varicella-zoster virus (VZV), Epstein-Barr virus, human herpesvirus-6 (HHV-6), human herpesvirus-7 (HHV-7), human herpesvirus-8 (HHV-8), pseudorabies and rhinotracheitis.

The compositions of the present invention may also be used topically in the treatment or prophylaxis of topical disease states mediated by or exacerbated by excessive cytokine production, such as inflamed joints, eczema, psoriasis and other inflammatory skin conditions such as sunburn; inflammatory eye conditions including conjunctivitis; pyresis, pain and other conditions associated with inflammation.

Periodontal disease has also been implemented in cytokine production, both topically and systemically. Hence, use of compositions of the present invention to control the inflammation associated with cytokine production in such peroral diseases such as gingivitis and periodontitis is another aspect of the present invention.

Finally, the compositions of the present invention may also be used to treat or prevent neurodegenerative disease selected from Alzheimer's disease, Parkinson's disease, amyotrophic lateral sclerosis, Huntington's disease, cerebral ischemia or neurodegenerative disease caused by traumatic injury, glutamate neurotoxicity or hypoxia.

In a preferred embodiment the compositions of the present invention may be used to treat or prevent a disease selected from chronic or acute inflammation, chronic inflammatory arthritis, rheumatoid arthritis, psoriasis, COPD, inflammatory bowel disease, septic shock, Crohn's disease, ulcerative colitis, multiple sclerosis and asthma.

Protein kinases are important enzymes involved in the regulation of many cellular functions. The LK6-serine/threonine-kinase gene of Drosophila melanogaster was described as a short-lived kinase which can associate with microtubules (J. Cell Sci. 1997, 110(2): 209-219). Genetic analysis in the development of the compound eye of Drosophila suggested a role in the modulation of the RAS signal pathway (Genetics 2000 156(3): 1219-1230). The closest human homologues of Drosophila LK6-kinase are the MAP-kinase interacting kinase 2 (Mnk2, e.g. the variants Mnk2a and Mnk2b) and MAP-kinase interacting kinase 1 (Mnk1) and variants thereof. These kinases are mostly localized in the cytoplasm. Mnks are phosphorylated by the p42 MAP kinases Erk1 and Erk2 and the p38-MAP kinases. This phosphorylation is triggered in a response to growth factors, phorbol esters and oncogenes such as Ras and Mos, and by stress signaling molecules and cytokines. The phosphorylation of Mnk proteins stimulates their kinase activity towards eukaryotic initiation factor 4E (eIF4E) (EMBO J. 16: 1909-1920, 1997; Mol Cell Biol 19, 1871-1880, 1990; Mol Cell Biol 21, 743-754, 2001). Simultaneous disruption of both, the Mnk1 and Mnk2 gene in mice diminishes basal and stimulated eIF4E phosphorylation (Mol Cell Biol 24, 6539-6549, 2004). Phosphorylation of eIF4E results in a regulation of the protein translation (Mol Cell Biol 22: 5500-5511, 2001).

There are different hypotheses describing the mode of the stimulation of the protein translation by Mnk proteins. Most publications describe a positive stimulatory effect on the cap-dependent protein translation upon activation of MAP kinase-interacting kinases. Thus, the activation of Mnk proteins can lead to an indirect stimulation or regulation of the protein translation, e.g. by the effect on the cytosolic phospholipase 2 alpha (BBA 1488:124-138, 2000).

WO 03/037362 discloses a link between human Mnk genes, particularly the variants of the human Mnk2 genes, and diseases which are associated with the regulation of body weight or thermogenesis. It is postulated that human Mnk genes, particularly the Mnk2 variants are involved in diseases such as e.g. metabolic diseases including obesity, eating disorders, cachexia, diabetes mellitus, hypertension, coronary heart disease, hypercholesterolemia, dyslipidemia, osteoarthritis, biliary stones, cancer of the genitals and sleep apnea, and in diseases connected with the ROS defense, such as e.g. diabetes mellitus and cancer. WO 03/03762 moreover discloses the use of nucleic acid sequences of the MAP kinase-interacting kinase (Mnk) gene family and amino acid sequences encoding these and the use of these sequences or of effectors of Mnk nucleic acids or polypeptides, particularly Mnk inhibitors and activators in the diagnosis, prophylaxis or therapy of diseases associated with the regulation of body weight or thermogenesis.

WO 02/103361 describes the use of kinases 2a and 2b (Mnk2a and Mnk2b) interacting with the human MAP kinase in assays for the identification of pharmacologically active ingredients, particularly useful for the treatment of diabetes mellitus type 2. Moreover, WO 02/103361 discloses also the prophylaxis and/or therapy of diseases associated with insulin resistance, by modulation of the expression or the activity of Mnk2a or Mnk2b. Apart from peptides, peptidomimetics, amino acids, amino acid analogues, polynucleotides, polynucleotide analogues, nucleotides and nucleotide analogues, 4-hydroxybenzoic acid methyl ester are described as a substance which binds the human Mnk2 protein.

Inhibitors of Mnk (referred to as CGP57380 and CGP052088) have been described (cf. Mol. Cell. Biol. 21, 5500, 2001; Mol Cell Biol Res Comm 3, 205, 2000; Genomics 69, 63, 2000). CGP052088 is a staurosporine derivative having an $IC_{50}$ of 70 nM for inhibition of in vitro kinase activity of Mnk1. CGP57380 is a low molecular weight selective, non-cytotoxic inhibitor of Mnk2 (Mnk2a or Mnk2b) or of Mnk1: The addition of CGP57380 to cell culture cells, transfected with Mnk2 (Mnk2a or Mnk2b) or Mnk1 showed a strong reduction of phosphorylated eIF4E.

First evidence for a role of Mnks in inflammation was provided by studies demonstrating activation of Mnk1 by proinflammatory stimuli. The cytokines TNFα and IL-1β trigger the activation of Mnk1 in vitro (Fukunaga and Hunter, EMBO J 16(8): 1921-1933, 1997) and induce the phosphorylation of the Mnk-specific substrate eIF4E in vivo (Ueda et al., Mol Cell Biol 24(15): 6539-6549, 2004). In addition, administration of lipopolysaccharide (LPS), a potent stimulant of the inflammatory response, induces activation of Mnk1 and Mnk2 in mice, concomitant with a phosphorylation of their substrate eIF4E (Ueda et al., Mol Cell Biol 24(15): 6539-6549, 2004).

Furthermore, Mnk1 has been shown to be involved in regulating the production of proinflammatory cytokines. Mnk1 enhances expression of the chemokine RANTES (Nikolcheva et al., J Clin Invest 110, 119-126, 2002). RANTES is a potent chemotractant of monocytes, eosinophils, basophiles and, natural killer cells. It activates and induces proliferation of T lymphocytes, mediates degranulation of basophils and induces the respiratory burst in eosinophils (Conti and DiGioacchino, Allergy Asthma Proc 22(3):133-7, 2001)

WO 2005/00385 and Buxade et al., Immunity 23: 177-189, August 2005 both disclose a link between Mnks and the control of TNFα biosynthesis. The proposed mechanism is mediated by a regulatory AU-rich element (ARE) in the TNFα mRNA. Buxade et al. demonstrate proteins binding and controlling ARE function to be phosphorylated by Mnk1 and Mnk2. Specifically Mnk-mediated phosphorylation of the ARE-binding protein hnRNP A1 has been suggested to enhance translation of the TNFα mRNA.

TNFα is not the only cytokine regulated by an ARE. Functional AREs are also found in the transcripts of several interleukins, interferones and chemokines (Khabar, J Interf Cytokine Res 25: 1-10, 2005). The Mnk-mediated phosphorylation of ARE-binding proteins has thus the potential to control biosynthesis of cytokines in addition to that of TNFα.

Current evidence demonstrates Mnks as down stream targets of inflammatory signalling as well as mediators of the inflammatory response. Their involvement in the production of TNFα, RANTES, and potentially additional cytokines suggests inhibition of Mnks as strategy for anti-inflammatory therapeutic intervention.

The problem underlying the present invention is to provide potent and selective Mnk1 and/or Mnk2 inhibitors which may effectively and safely be used for the treatment of metabolic diseases, inflammatory diseases and their consecutive complication and disorders.

It has now been surprisingly found that certain pyrrolopyrimidine compounds are potent inhibitors of the kinase enzymes Mnk1 and/or Mnk2 and/or variants thereof and as such may be useful in the prophylaxis and/or therapy of diseases which can be influenced by the inhibition of the kinase activity of Mnk1 and/or Mnk2 (Mnk2a or Mnk2b) and/or variants thereof.

Pyrrolopyrimidine compounds of the present invention are compounds of the general formula (1):

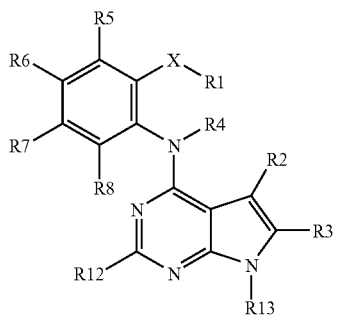

wherein X is a single bond, O, S, $SO_2$, $CH_2$, $CHR_{1a}$, $CR_{1a}R_{1b}$, CH(halogen), C(halogen)$_2$, C=O, C(O)NR$_{1a}$, NH or NR$_{1a}$, wherein $R_{1a}$ and $R_{1b}$ are $C_{1-6}$ alkyl, $C_{1-6}$ alkyl $C_{3-10}$ cycloalkyl, $C_{3-10}$ cycloalkyl, $C_{1-6}$ alkyl 3 to 10 membered heterocycloalkyl comprising at least one heteroatom selected from N, S and O, 3 to 10 membered heterocycloalkyl comprising at least one heteroatom selected from N, S and O, wherein $R_{1a}$ and $R_{1b}$ are optionally substituted with one or more $R_9$;

$R_1$ is hydrogen, $C_{1-6}$ alkyl, $C_{1-6}$ alkyl $C_{3-10}$ cycloalkyl, $C_{3-10}$ cycloalkyl, $C_{1-6}$ alkyl 3 to 10 membered heterocycloalkyl comprising at least one heteroatom selected from N, S and O, 3 to 10 membered heterocycloalkyl comprising at least one heteroatom selected from N, S and O, $C_{6-10}$ aryl, $C_{1-6}$ alkyl $C_{6-10}$ aryl, $C_{5-10}$ heteroaryl comprising at least one heteroatom selected from N, S and O, $C_{1-6}$ alkyl $C_{5-10}$ heteroaryl comprising at least one heteroatom selected from N, S and O, wherein $R_1$ is optionally substituted with one or more $R_9$;

or if X is $NR_{1a}$, $CHR_{1a}$, $C(O)NR_{1a}$ or $CR_{1a}R_{1b}$, $R_1$ may form a carbocyclic or heterocyclic ring with $R_{1a}$ and the N or C atom to which they are attached, which may contain one or more additional heteroatoms selected from N, S and O, which may be substituted with one or more $R_9$;

$R_2$ and $R_3$ are the same or different and are independently selected from hydrogen, $C_{1-6}$ alkyl, $C_{1-6}$ alkyl $C_{3-10}$ cycloalkyl, $C_{3-10}$ cycloalkyl, $C_{6-10}$ aryl, $C_{1-6}$ alkyl $C_{6-10}$ aryl, $C_{5-10}$ heteroaryl comprising at least one heteroatom selected from N, S and O, $C_{1-6}$ alkyl $C_{5-10}$ heteroaryl comprising at least one heteroatom selected from N, S and O, $C_{1-6}$ alkyl 3 to 10 membered heterocycloalkyl comprising at least one heteroatom selected from N, S and O, 3 to 10 membered heterocycloalkyl comprising at least one heteroatom selected from N, S and O, or together with the C atoms that they are attached to form a $C_{3-7}$ cycloalkyl or a 3 to 10 membered heterocloalkyl group, wherein $R_2$ and $R_3$ are optionally substituted with one or more $R_9$, $R_2$ may also be $R_9$ and $R_3$ may also be $R_{10}$;

$R_4$ is hydrogen, $C_{1-4}$ alkyl, urea, thiourea or acetyl optionally substituted with one or more $R_9$;

or $R_4$ may form a 5 or 6 membered heterocyclic ring with $R_1$;

$R_5$, $R_6$, $R_7$ and $R_8$ are the same or different and are independently selected from H or $R_9$;

$R_9$ is independently halogen; CN; $COOR_{11}$; $OR_{11}$; C(O)N($R_{11}R_{11a}$); $S(O)_2N(R_{11}R_{11a})$; $S(O)N(R_{11}R_{11a})$; $S(O)_2R_{11}$; $N(R_{11})S(O)_2N(R_{11a}R_{11b})$; $SR_{11}$; $N(R_{11}R_{11a})$; $OC(O)R_{11}$; $N(R_{11})C(O)R_{11a}$; $N(R_{11})S(O)_2R_{11a}$; $N(R_{11})S(O)R_{11a}$; $N(R_{11})C(O)N(R_{11a}R_{11b})$; $N(R_{11})C(O)OR_{11a}$; $OC(O)N(R_{11}R_{11a})$; oxo (=O), where the ring is at least partially saturated; $C(O)R_{11}$; $C_{1-6}$ alkyl; phenyl; $C_{3-7}$ cycloalkyl; or heterocyclyl, wherein $C_{1-6}$ alkyl; phenyl; $C_{3-7}$ cycloalkyl; and heterocyclyl are optionally substituted with one or more $R_{10}$;

$R_{10}$ is independently halogen; CN; $OR_{11}$; $S(O)_2N(R_{11}R_{11a})$; $S(O)N(R_{11}R_{11a})$; $S(O)_2R_{11}$; $N(R_{11})S(O)_2N(R_{11a}R_{11b})$; $SR_{11}$; $N(R_{11}R_{11a})$; $OC(O)R_{11}$; $N(R_{11})C(O)R_{11a}$; $N(R_{11})S(O)_2R_{11a}$; $N(R_{11})S(O)R_{11a}$; $N(R_{11})C(O)N(R_{11a}R_{11b})$; $N(R_{11})C(O)OR_{11a}$; $OC(O)N(R_{11}R_{11a})$; oxo (=O), where the ring is at least partially saturated; $C(O)R_{11}$; $C_{1-6}$ alkyl; phenyl; $C_{3-7}$ cycloalkyl; or heterocyclyl, wherein $C_{1-6}$ alkyl; phenyl; $C_{3-7}$ cycloalkyl; and heterocyclyl are optionally substituted with one or more $R_9$;

$R_{11}$, $R_{11a}$, $R_{11b}$ are independently selected from the group consisting of hydrogen, $C_{1-6}$ alkyl, $C_{1-6}$ alkyl $C_{3-10}$ cycloalkyl, $C_{3-10}$ cycloalkyl, $C_{1-6}$ alkyl 3 to 10 membered heterocycloalkyl comprising at least one heteroatom selected from N, S and O, 3 to 10 membered heterocycloalkyl comprising at least one heteroatom selected from N, S and O, $C_{6-10}$ aryl, 5 to 10 membered heteroaryl comprising at least one heteroatom selected from N, S and O, wherein $R_{11}$, $R_{11a}$, $R_{11b}$ are optionally substituted with one or more $R_9$;

$R_{12}$ is hydrogen, halogen, OH, $NH_2$, $C(O)NH_2$ or $C_{1-6}$ alkyl;

$R_{13}$ is hydrogen, $C_{1-6}$ alkyl, $C_{1-6}$ alkyoxycarbonyl, $C_{6-10}$ aryloxycarbonyl, $C_{6-10}$ aralkoxycarbonyl, carbamoyl or acyl;

or a metabolite, prodrug or a pharmaceutically acceptable salt thereof.

The compounds as defined in claim 3 are particularly preferred.

Further preferred embodiments are:

Compounds, wherein X is a single bond, O, S, $SO_2$, $CH_2$, $CHR_{1a}$, $CR_{1a}R_{1b}$, CH(halogen), C(halogen)$_2$, C=O, C(O)NR$_{1a}$, NH or NR$_{1a}$, wherein $R_{1a}$ and $R_{1b}$ are $C_{1-6}$ alkyl, $C_{1-6}$ alkyl $C_{3-10}$ cycloalkyl, $C_{3-10}$ cycloalkyl, $C_{1-6}$ alkyl 3 to 10 membered heterocycloalkyl comprising at least one heteroatom selected from N, S and O, 3 to 10 membered heterocycloalkyl comprising at least one heteroatom selected from N, S and O, wherein $R_{1a}$ and $R_{1b}$ are optionally substituted with one or more $R_9$;

$R_1$ is hydrogen, $C_{1-6}$ alkyl, $C_{1-6}$ alkyl $C_{3-10}$ cycloalkyl, $C_{3-10}$ cycloalkyl, $C_{1-6}$ alkyl 3 to 10 membered heterocycloalkyl comprising at least one heteroatom selected from N, S and O, 3 to 10 membered heterocycloalkyl comprising at least one heteroatom selected from N, S and O, $C_{6-10}$ aryl, $C_{1-6}$ alkyl $C_{6-10}$ aryl, $C_{5-10}$ heteroaryl comprising at least one heteroatom selected from N, S and O, $C_{1-6}$ alkyl $C_{5-10}$ heteroaryl comprising at least one heteroatom selected from N, S and O, wherein $R_1$ is optionally substituted with one or more $R_9$;

or if X is $NR_{1a}$, $CHR_{1a}$, $C(O)NR_{1a}$ or $CR_{1a}R_{1b}$, $R_1$ may form a carbocyclic or heterocyclic ring with $R_{1a}$ and the N or C atom to which they are attached, which may contain one or more additional heteroatoms selected from N, S and O, which may be substituted with one or more $R_9$;

$R_2$ and $R_3$ are the same or different and are independently selected from hydrogen, methyl, phenyl, ethyl, propyl, perfluoromethyl, or form together with the C atoms to which they are attached a 5-membered carbocyclic ring;

$R_4$ is hydrogen or $C_{1-4}$ alkyl;

$R_5$, $R_6$, $R_7$ and $R_8$ are the same or different and are independently selected from hydrogen, $CONH_2$, $CO_2H$, $CO_2CH_3$, Cl and F, or a metabolite, prodrug or pharmaceutically acceptable salt thereof.

Compounds, wherein X is a single bond, O, S, $SO_2$, $CH_2$, $CHR_{1a}$, $CR_{1a}R_{1b}$, CH(halogen), C(halogen)$_2$, C=O, $C(O)NR_{1a}$, NH or $NR_{1a}$, wherein $R_{1a}$ and $R_{1b}$ are $C_{1-6}$ alkyl;

$R_1$ is hydrogen, methyl, ethyl, propyl, butyl, difluoromethyl, bromoethyl, 1,1,2,2-tetrafluoroethyl, 1,1,1-trifluoropropyl, perfluoromethyl, cyclopropylmethyl, cyclopentyl, cyclohexyl, adamantyl, norbonanyl, tetrahydrofuranyl, tetrahydropyranyl, phenyl or pyrrolidin-3-yl substituted at the nitrogen with $R_9$;

or if X is $NR_{1a}$, $R_1$ forms a morpholino group, a pyrrolidino group or a piperidino group together with $R_{1a}$ and the N atom to which they are attached, which may be substituted with —$CH_3$ or —$C(O)OC_4H_9$;

$R_2$ and $R_3$ are the same or different and are independently selected from hydrogen, methyl, phenyl, ethyl, propyl, perfluoromethyl, or form together with the C atoms to which they are attached a 5-membered carbocyclic ring;

$R_4$ is hydrogen or $C_{1-4}$ alkyl;

$R_5$, $R_6$, $R_7$ and $R_8$ are the same or different and are independently selected from hydrogen, $CONH_2$, $CO_2H$, $CO_2CH_3$, Cl and F;

or a metabolite, prodrug or pharmaceutically acceptable salt thereof.

Compounds, wherein $R_2$ and $R_3$ are the same or different and are selected from methyl, hydrogen and perfluoromethyl.

Compounds, wherein X is a single bond, O, S, $SO_2$, $CH_2$, $CHR_{1a}$, $CR_{1a}R_{1b}$, CH(halogen), C(halogen)$_2$, C=O, $C(O)NR_{1a}$, NH or $NR_{1a}$, wherein $R_{1a}$ and $R_{1b}$ are $C_{1-6}$ alkyl;

$R_1$ is hydrogen, $C_{1-6}$ alkyl, $C_{1-6}$ alkyl $C_{3-10}$ cycloalkyl, $C_{3-10}$ cycloalkyl, 5 to 10 membered heterocyclyl comprising at least one heteroatom selected from N, S and O, $C_{6-10}$ aryl, $C_{1-6}$ alkyl $C_{6-10}$ aryl, $C_{5-10}$ heteroaryl comprising at least one heteroatom selected from N, S and O, $C_{1-6}$ alkyl $C_{5-10}$ heteroaryl comprising at least one heteroatom selected from N, S and O, wherein $R_1$ is optionally substituted with one or more $R_9$;

or if X is $NR_{1a}$, $R_1$ may form a heterocyclic ring together with $R_{1a}$ and the N atom to which they are attached, which may contain an additional heteroatom selected from N, S and O, which may be substituted with one or more $R_9$;

$R_2$ and $R_3$ are the same or different and are independently selected from hydrogen, $C_{1-4}$ alkyl which may optionally be substituted with one or more halogen atoms, an acetyl group, a urea, a hydroxyl, a phenyl group and an amino group or form together with the C atoms to which they are attached a $C_{3-6}$ cycloalkyl group;

$R_4$ is hydrogen or $C_{1-4}$ alkyl;

$R_5$, $R_6$, $R_7$ and $R_8$ are the same or different and are independently selected from hydrogen, $CO_2H$, $CO_2R_{1c}$, $CONH_2$, $CONHR_{1d}$ and halogen, whereby $R_{1c}$ and $R_{1d}$ are $C_{1-6}$ alkyl;

or a metabolite, prodrug or pharmaceutically acceptable salt thereof.

Compounds, wherein $R_4$ is hydrogen.

Compounds, wherein X is O or a single bond.

Compounds, wherein the cycloalkyl group is adamantyl or norbonanyl, cyclohexyl or cyclopentyl.

Compounds, wherein the halogen atom is selected from Cl, Br and F.

Compounds, wherein $R_5$, $R_6$, $R_7$ and $R_8$ are hydrogen.

Compounds, wherein at least one of $R_5$, $R_6$, $R_7$ and $R_8$ is F, $CONH_2$ or $CO_2CH_3$.

Compounds, wherein $R_1$ is hydrogen, methyl, ethyl, propyl, butyl, difluoromethyl, bromoethyl, 1,1,2,2-tertrafluoroethyl, 1,1,1-trifluoropropyl, perfluoromethyl, cyclopropylmethyl, cyclopentyl, cyclohexyl, adamantyl, norbonanyl, tetrahydrofuranyl, tetrahydropyranyl, phenyl or pyrrolidin-3-yl substituted at the nitrogen with $R_9$, wherein $R_9$ is as defined in claim 1.

Compounds, wherein $R_4$, $R_7$ and $R_8$ are hydrogen.

Compounds, wherein $R_6$ is $C(O)NH_2$.

Compounds, wherein $R_4$, $R_7$ and $R_8$ are hydrogen and $R_6$ is $C(O)NH_2$.

Compounds, wherein $R_6$ is $C(O)NH_2$, $R_1$ is selected from $C_{3-7}$ cycloalkyl, $C_{1-6}$ alkyl and a 3 to 10 membered heterocycloalkyl group comprising at least one heteroatom selected from N,S and O and $R_{12}$ is hydrogen.

Compounds, wherein $R_6$ is $C(O)NH_2$, $R_1$ is selected from $C_{3-7}$ cycloalkyl, $C_{1-6}$ alkyl and a 3 to 10 membered heterocycloalkyl group comprising at least one heteroatom selected from N,S and O and $R_4$, $R_7$, $R_8$ and $R_{12}$ are hydrogen.

Preferred compounds are selected from:

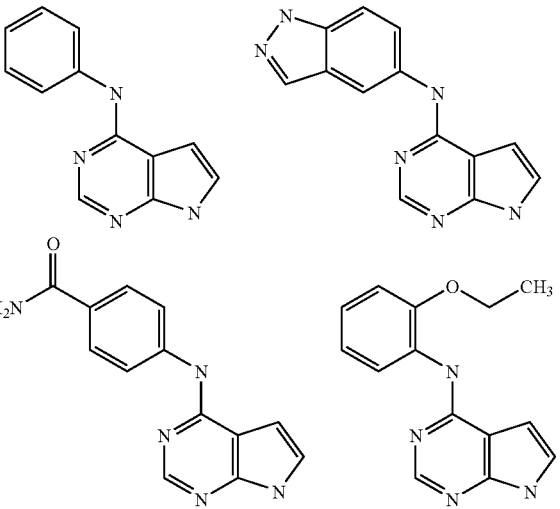

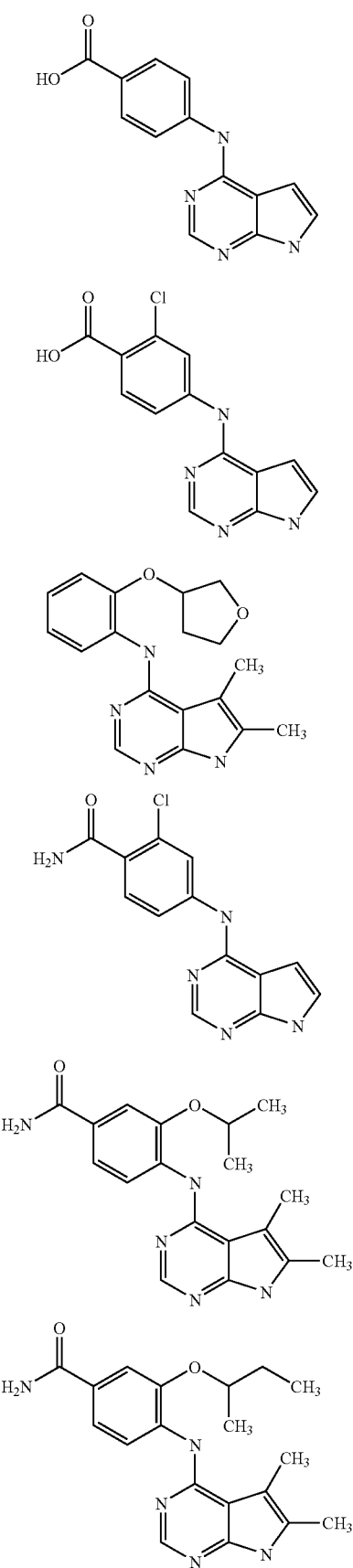
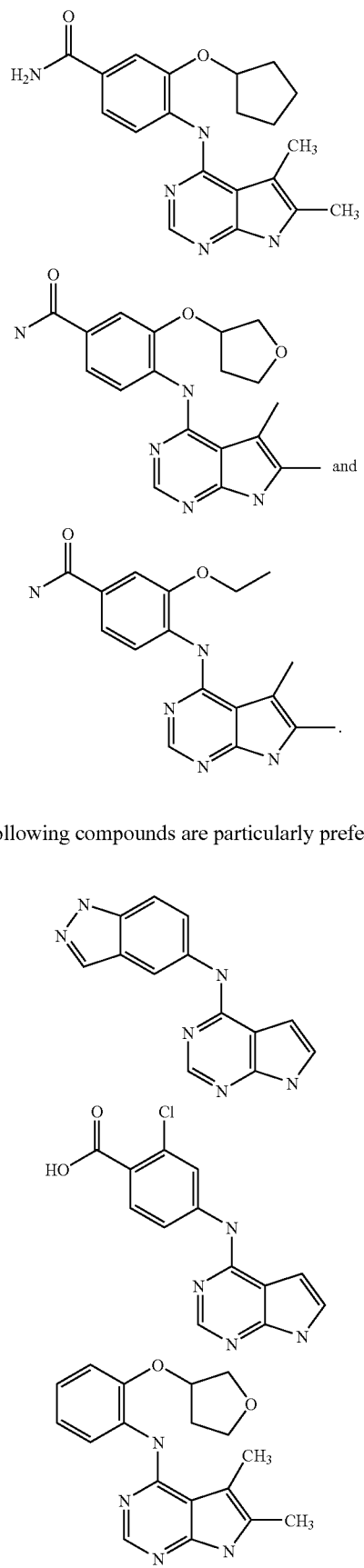
The following compounds are particularly preferred

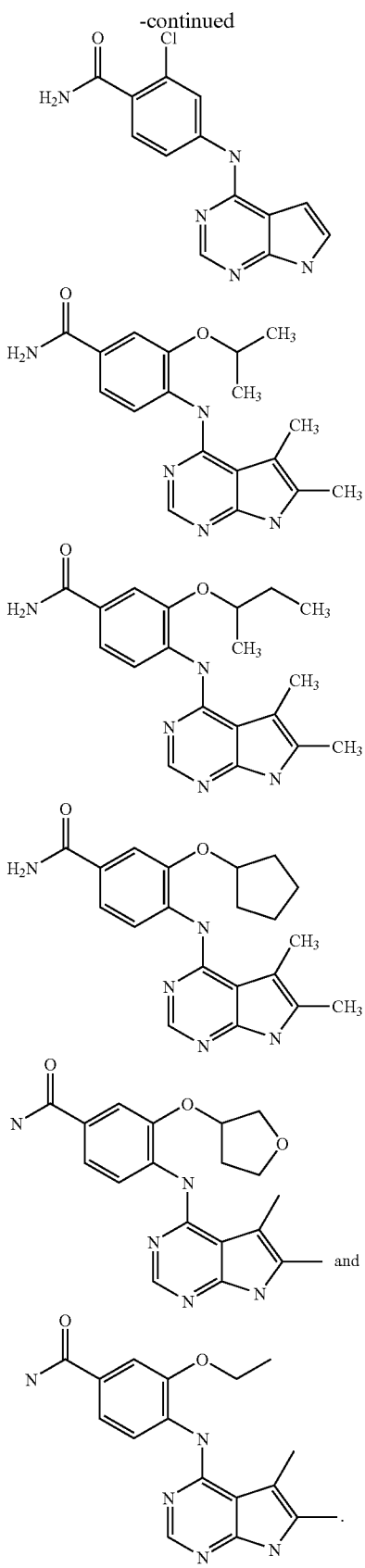

Typical methods of preparing the compounds of the invention are described below in the experimental section.

The potent inhibitory effect of the compounds of the invention may be determined by in vitro enzyme assays as described in the Examples in more detail.

Pharmaceutically acceptable salts of the compounds of the invention of formula (1) can be formed with numerous organic and inorganic acids and bases. Exemplary acid addition salts including acetate, adipate, alginate, ascorbate, aspartate, benzoate, benzenesulfonate, bisulfate, borate, butyrate, citrate, camphorate, camphersulfonate, cyclopentanepropionate, digluconate, dodecyl sulfate, ethane sulfonate, fumarate, glucoheptanoate, glycerophosphate, hemisulfate, heptanoate, hexanoate, hydrochloride, hydrobromide, hydroiodide, 2-hydroxyethane sulfonate, lactate, maleate, methane sulfonate, 2-naphthalene sulfonate, nicotinate, nitrate, oxalate, pamoate, pectinate, persulfate, 3-phenyl sulfonate, 3-phenylpropionate, phosphate, picrate, pivalate, propionate, salicylate, succinate, sulfate, sulfonate, tartrate, thiocyanate, toluene sulfonate such as tosylate, undecanoate, or the like.

Basic nitrogen-containing moieties can be quaternized with such agents as lower alkyl halides, such as methyl, ethyl, propyl, and butyl chloride, bromide and iodide; dialkyl sulfates like dimethyl, diethyl, dibutyl, and diamyl sulfates, long-chain alkyl halides such as decyl, lauryl, myristyl and stearyl chloride, bromide and iodide, or aralkyl halides like benzyl and phenethyl bromides, or others. Water soluble or dispersible products are thereby obtained.

Pharmaceutically acceptable basic addition salts include but are not limited to cations based on the alkaline and alkaline earth metals such as sodium, lithium, potassium, calcium, magnesium, aluminum salts and the like, as well as non toxic ammonium quarternary ammonium, and amine cations, including but not limited to ammonium, tetramethylammonium, tetraethylammonium, methylamine, dimethylamine, trimethylamine, triethylamine, ethylamine and the like. Other representative amines useful for the formation of base addition salts include benzazethine, dicyclohexyl amine, hydrabine, N-methyl-D-glucamine, N-methyl-D-glucamide, t-butyl amine, diethylamine, ethylendiamine, ethanolamine, diethanolamine, piperazine and the like and salts with amino acids such as arginine, lysine, or the like.

Compounds of the formula (1) can be present as tautomers. The present invention comprises all tautomeric forms. Furthermore, the present invention also comprises all stereoisomers of the compounds according to the invention, including its enantiomers and diastereomers. Individual stereoisomers of the compounds according to the invention can be substantially present pure of other isomers, in admixture thereof or as racemates or as selected stereoisomers.

As used herein the term "metabolite" refers to (i) a product of metabolism, including intermediate and products, (ii) any substance involved in metabolism (either as a product of metabolism or as necessary for metabolism), or (iii) any substance produced or used during metabolism. In particular it refers to the end product that remains after metabolism.

As used herein the term "prodrug" refers to (i) an inactive form of a drug that exerts its effects after metabolic processes within the body convert it to a usable or active form, or (ii) a substance that gives rise to a pharmacologically active metabolite, although not itself active (i.e. an inactive precursor).

As used herein the term "$C_{3-10}$ cycloalkyl" refers to mono- or polycyclic carbocyclic alkyl substituent or group having 3 to 10 ring atoms, such as cyclopropyl, cyclobutyl, cyclopentyl, cyclohexyl, cycloheptyl, cyclobutenyl, cyclopentenyl, cyclopentadienyl, cyclohexenyl, cyclohexadienyl, cycloheptenyl, cycloheptadienyl, cycloheptatrienyl perhydrated naphthalene or indene, adamantyl or norbonanyl and the like.

The term "$C_{1-6}$ alkyl" as used herein alone or in combination with other terms such as in alkoxy or acyl refers to a $C_{1-6}$, preferably $C_{1-4}$ straight or branched alkyl/alkoxy group such as methyl, ethyl, propyl (iso-, n-), butyl (iso-, n-, sec-, tert-), pentyl, hexyl, methoxy, ethoxy, propoxy (iso-, n-), butoxy (iso-, n-, sec-, tert-), pentoxy, hexoxy; moreover, the term "$C_{1-6}$ alkyl" also includes an alkyl group which may contain oxygen in the chain and may be substituted with halogen to form an ether or halogenated ether group.

The term "acyl" as used herein refers to a $C_{1-6}$, preferably $C_{1-4}$ alkyl carbonyl group.

The term "halogen" refers to a halogen atom selected from fluorine, chlorine, bromine, iodine, preferably fluorine and chlorine, more preferably fluorine.

The term "aryl" refers to a mono- or bicyclic aromatic group having 6 to 10 backbone carbon atoms, wherein optionally one of the rings of the bicyclic structure is aromatic and the other is a carbocyclic group, such as phenyl, 1-naphthyl, 2-naphthyl, indenyl, indanyl, azulenyl, fluorenyl, 1,2,3,4-tetrahydronaphthyl.

The term "heterocyclyl" refers to monocyclic saturated or unsaturated heterocyclyl groups with 1 to 4 hetero atoms selected from N, S and O, with the remainder of the ring atoms being carbon atoms and having preferably a total number of ring atoms of 3 to 10, such as morpholino, piperazinyl, piperidinyl, pyridyl, pyrimidinyl, thiazolyl, indolyl, imidazolyl, oxadiazolyl, tetrazolyl, pyrazinyl, triazolyl, thiophenyl or furanyl.

The term "heteroaryl" refers to a mono- or bicyclic aromatic group with 1 to 4 hetero atoms selected from N, S and O, with the remainder of the ring atoms being carbon atoms and having preferably a total number of ring atoms of 5 to 10. Examples without limitation of heteroaryl groups are such as benzofuranyl, furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, quinolinyl, isoquinolinyl, purinyl, carbazolyl, benzoxazolyl, benzamidazolyl, indolyl, isoindolyl, pyrazinyl, diazinyl, pyrazine, triazinyltriazine, tetrazinyl, tetrazolyl, benzothiophenyl, benzopyridyl and benzimidazolyl.

In a further aspect the present invention provides pharmaceutical compositions comprising a pyrrolopyrimidine compound of the present invention and optionally a pharmaceutically acceptable carrier.

The pharmaceutical composition according to the present invention may further comprise an additional therapeutic agent. Particularly preferred are compositions, wherein the additional therapeutic agent is selected from antidiabetics like insulin, long and short acting insulin analogues, sulfonylureas and other antidiabetics derived from thiazolidindiones, lipid lowering agents such as statines, fibrates, ion exchange resins, nicotinic acid derivatives, or HMG-CoA reductase inhibitors, cardiovascular therapeutics such as nitrates, antihypertensiva such as β-blockers, ACE inhibitors, Ca-channel blockers, angiotensin II receptor antagonists, diuretics, thrombocyte aggregation inhibitors, or antineoplastic agents such as alkaloids, alkylating agents, antibiotics, or antimetabolites, or anti-obesity agents. Further preferred compositions are compositions wherein the additional therapeutic agent is selected from a histamine antagonist, a bradikinin antagonist, serotonin antagonist, leukotriene, an anti-asthmatic, an NSAID, an antipyretic, a corticosteroid, an antibiotic, an analgetic, a uricosuric agent, chemotherapeutic agent, an anti gout agent, a bronchodilator, a cyclooxygenase-2 inhibitor, a steroid, a 5-lipoxygenase inhibitor, an immunosuppressive agent, a leukotriene antagonist, a cytostatic agent, antibodies or fragments thereof against cytokines and soluble parts (fragments) of cytokine receptors.

More particularly preferred are compounds such as human NPH insulin, human lente or ultralente insulin, insulin Lispro, insulin Asptart, or insulin Glargine, atenolol, bisoprolol, metoprolol, esmolol, celiprolol, talinolol, oxprenolol, pindolol, propanolol, bupropanolol, penbutolol, mepindolol, sotalol, certeolol, nadolol, carvedilol, nifedipin, nitrendipin, amlodipin, nicardipin, nisoldipin, diltiazem, enalapril, verapamil, gallopamil, quinapril, captopril, lisinopril, benazepril, ramipril, peridopril, fosinopril, trandolapril, irbesatan, losartan, valsartan, telmisartan, eprosartan, olmesartan, hydrochlorothiazide, piretanid, chlorotalidone, mefruside, furosemide, bendroflumethiazid, triamterene, dehydralazine, acetylsalicylic acid, tirofiban-HCl, dipyramidol, triclopidin, iloprost-trometanol, eptifibatide, clopidogrel, piratecam, abciximab, trapidil, simvastatine, bezafibrate, fenofibrate, gemfibrozil, etofyllin, clofibrate, etofibrate, fluvastatine, lovastatine, pravastatin, colestyramide, colestipol-HCl, xantinol nicotinat, inositol nicotinat, acipimox, nebivolol, glycerolnitrate, isosorbide mononitrate, isosorbide dinitrate, pentaerythrityl tetranitrate, indapamide, cilazepril, urapidil, eprosartan, nilvadipin, metoprolol, doxazosin, molsidormin, moxaverin, acebutolol, prazosine, trapidil, clonidine, vinca alkaloids and analogues such as vinblastin, vincristin, vindesin, vinorelbin, podophyllotoxine derivatives, etoposid, teniposid, alkylating agents, nitroso ureas, N-lost analogues, cycloplonphamid, estamustin, melphalan, ifosfamid, mitoxantron, idarubicin, doxorubicin, bleomycin, mitomycin, dactinomycin, daptomycin, antimetabolites such as cytarabin, fluorouracil, fluoroarabin, gemcitabin, tioguanin, capecitabin, combinations such as adriamycin/daunorubicin, cytosine arabinosid/cytarabine, 4-HC, or other phosphamides.

Other particularly preferred compounds are compounds such as clemastine, diphenhydramine, dimenhydrinate, promethazine, cetirizine, astemizole, levocabastine, loratidine, terfenadine, acetylsalicylic acid, sodoum salicylate, salsalate, diflunisal, salicylsalicylic acid, mesalazine, sulfasalazine, osalazine, acetaminophen, indomethacin, sulindac, etodolac, tolmetin, ketorolac, bethamethason, budesonide, chromoglicinic acid, dimeticone, simeticone, domperidone, metoclopramid, acemetacine, oxaceprol, ibuprofen, naproxen, ketoprofen, flubriprofen, fenoprofen, oxaprozin, mefenamic acid, meclofenamic acid, pheylbutazone, oxyphenbutazone, azapropazone, nimesulide, metamizole, leflunamide, eforicoxib, lonazolac, misoprostol, paracetamol, aceclofenac, valdecoxib, parecoxib, celecoxib, propyphenazon, codein, oxapozin, dapson, prednisone, prednisolon, triamcinolone, dexibuprofen, dexamethasone, flunisolide, albuterol, salmeterol, terbutalin, theophylline, caffeine, naproxen, glucosamine sulfate, etanercept, ketoprofen, adalimumab, hyaluronic acid, indometacine, proglumetacine dimaleate, hydroxychloroquine, chloroquine, infliximab, etofenamate, auranofin, gold, [$^{224}$Ra]radium chloride, tiaprofenic acid, dexketoprofen(trometamol), cloprednol, sodium aurothiomalate aurothioglucose, colchicine, allopurinol, probenecid, sulfinpyrazone, benzbromarone, carbamazepine, lornoxicam, fluorcortolon, diclofenac, efalizumab, idarubicin, doxorubicin, bleomycin, mitomycin, dactinomycin, daptomycin, cytarabin, fluorouracil, fluoroarabin, gemcitabin, tioguanin, capecitabin, adriamydin/daunorubicin, cytosine arabinosid/cytarabine, 4-HC, or other phosphamides, penicillamine, a hyaluronic acid preparation, arteparon, glucosamine, MTX, soluble fragments of the TNF-receptor (such as etanercept (Enbrel)) and antibodies against TNF (such as infliximab (Remicade), natalizumab (Tysabri) and adalimumab (Humira)).

It will be appreciated by the person of ordinary skill in the art that the compounds of the invention and the additional therapeutic agent may be formulated in one single dosage form, or may be present in separate dosage forms and may be either administered concomitantly (i.e. at the same time) or sequentially.

The pharmaceutical compositions of the present invention may be in any form suitable for the intended method of administration.

The compounds of the present invention may be administered orally, parenterally, such as bronchopulmonary, subcutaneously, intravenously, intramuscularly, intraperitoneally, intrathecally, transdermally, transmucosally, subdurally, locally or topically via iontopheresis, sublingually, by inhalation spray, aerosol or rectally and the like in dosage unit formulations optionally comprising conventional pharmaceutically acceptable excipients.

Excipients that may be used in the formulation of the pharmaceutical compositions of the present invention comprise carriers, vehicles, diluents, solvents such as monohydric alcohols such as ethanol, isopropanol and polyhydric alcohols such as glycols and edible oils such as soybean oil, coconut oil, olive oil, safflower oil cottonseed oil, oily esters such as ethyl oleate, isopropyl myristate; binders, adjuvants, solubilizers, thickening agents, stabilizers, disintergrants, glidants, lubricating agents, buffering agents, emulsifiers, wetting agents, suspending agents, sweetening agents, colorants, flavors, coating agents, preservatives, antioxidants, processing agents, drug delivery modifiers and enhancers such as calcium phosphate, magnesium state, talc, monosaccharides, disaccharides, starch, gelatine, cellulose, methylcellulose, sodium carboxymethyl cellulose, dextrose, hydroxypropyl-β-cyclodextrin, polyvinylpyrrolidone, low melting waxes, ion exchange resins.

Other suitable pharmaceutically acceptable excipients are described in Remington's Pharmaceutical Sciences, 15$^{th}$ Ed., Mack Publishing Co., New Jersey (1991).

Dosage forms for oral administration include tablets, capsules, lozenges, pills, wafers, granules, oral liquids such as syrups, suspensions, solutions, emulsions, powder for reconstitution.

Dosage forms for parenteral administration include aqueous or olageous solutions or emulsions for infusion, aqueous or olageous solutions, suspensions or emulsions for injection pre-filled syringes, and/or powders for reconstitution.

Dosage forms for local/topical administration comprise insufflations, aerosols, metered aerosols, transdermal therapeutic systems, medicated patches, rectal suppositories, and/or ovula.

The amount of the compound of the present invention that may be combined with the excipients to formulate a single dosage form will vary upon the host treated and the particular mode of administration.

The pharmaceutical compositions of the invention can be produced in a manner known per se to the skilled person as described, for example, in Remington's Pharmaceutical Sciences, 15$^{th}$ Ed., Mack Publishing Co., New Jersey (1991).

In a further aspect of the invention the use of a pyrrolopyrimidine compound of the present invention for the production of a pharmaceutical composition for inhibiting the activity of the kinase activity of Mnk1 or Mnk2 (Mnk2a, Mnk2b) or further variants thereof is provided, in particular for the prophylaxis or therapy of metabolic diseases, hematopoietic disorders, cancer and their consecutive complications and disorders. Whereby the prophylaxis and therapy of metabolic diseases of the carbohydrate and/or lipid metabolism is preferred.

Diseases of the invention that are influenced by the inhibition of the kinase activity of Mnk1 and/or Mnk2 (Mnk2a or Mnk2b) and/or further variants thereof include diseases related to the regulation of metabolic diseases, such as obesity, eating disorders, cachexia, diabetes mellitus, metabolic syndrome, hypertension, coronary heart diseases, hypercholesterolemia, dyslipidemia, osteoarthritis, biliary stones and/or sleep apnea and diseases related to reactive oxygen compounds (ROS defense) such as diabetes mellitus, neurodegenerative diseases and cancer.

The pharmaceutical compositions of the invention are particularly useful for prophylaxis and treatment of obesity, diabetes mellitus and other metabolic diseases of the carbohydrate and lipid metabolism as stated above, in particular diabetes mellitus and obesity.

Thus in a more preferred embodiment of this invention the use of a pyrrolopyrimidine compound for the production of a pharmaceutical composition for the prophylaxis or therapy of metabolic diseases is provided.

As discussed above the compounds and compositions of the present invention are useful for the treatment and/or prophylaxis of hematopoetic disorders and their consecutive complications and disorders such as acute myeloid leukemia (AML), Morbus Hodgkin, Non-Hodgkin's lymphoma; hematopoetic disease, acute non-lymphocytic leukemia (ANLL), myeloproliferative disease acute promyelocytic leukemia (APL), acute myelomonocytic leukemia (AM-MoL), polycythemia vera, lymphoma, acute lymphocytic leukemia (ALL), chronic lymphocytic leukemia (CCL), Wilm's tumor, or Ewing's Sarcoma. In accordance with the invention the compounds and compositions of the present invention are useful in hematopoetic stem cell therapy.

In a further embodiment of the present invention the compounds and compositions of the present invention are useful for the treatment and/or prophylaxis of cancer and consecutive complications and disorders such as cancer of the upper gastrointestinal tract, pancreatic carcinoma, breast cancer, colon cancer, ovarian carcinoma, cervix carcinoma, corpus carcinoma, brain tumor, testicular cancer, laryngeal carcinoma, osteocarcinoma, prostatic cancer, retinoblastoma, liver carcinoma, lung cancer, neuroblastoma, renal carcinoma, thyroid carcinoma, esophageal cancer, soft tissue sarcoma, cachexia, or pain.

In yet a further aspect of the invention the use of a pyrrolopyrimidine compound of the invention for the production of a pharmaceutical composition for treating or preventing a cytokine mediated disorder such as an inflammatory disease.

The pharmaceutical compositions of the invention are thus useful for the prophylaxis or therapy of inflammatory diseases, in particular chronic or acute inflammation, chronic inflammatory arthritis, rheumatoid arthritis, psoriatic arthritis, osteoarthritis, juvenile rheumatoid arthritis, gouty arthritis; psoriasis, erythrodermic psoriasis, pustular psoriasis, inflammatory bowel disease, Crohn's disease and related conditions, ulcerative colitis, colitis, diverticulitis, nephritis, urethritis, salpingitis, oophoritis, endomyometritis, spondylitis, systemic lupus erythematosus and related disorders, multiple sclerosis, asthma, meningitis, myelitis, encephalomyelitis, encephalitis, phlebitis, thrombophlebitis, chronic obstructive disease (COPD), inflammatory lung disease, allergic rhinitis, endocarditis, osteomyelitis, rheumatic fever, rheumatic pericarditis, rheumatic endocarditis, rheumatic myocarditis, rheumatic mitral valve disease, rheumatic aortic valve disease, prostatitis, prostatocystitis, spondoarthropathies ankylosing spondylitis, synovitis, tenosynovotis, myositis, pharyngitis, polymyalgia rheumatica, shoulder tendonitis or bursitis, gout, pseudo gout, vasculitides, inflammatory diseases of the thyroid selected from granulomatous thyroiditis, lymphocytic thyroiditis, invasive fibrous thyroiditis, acute thyroiditis; Hashimoto's thyroiditis, Kawasaki's disease, Raynaud's phenomenon, Sjogren's syndrome, neuroinflammatory disease, sepsis, conjubctivitis, keratitis, iridocyclitis, optic neuritis, otitis, lymphoadenitis, nasopaharingitis, sinusitis, pharyngitis, tonsillitis, laryngitis, epiglottitis, bronchitis, pneumonitis, stomatitis, gingivitis, oesophagitis, gastritis, peritonitis, hepatitis, cholelithiasis, cholecystitis, glomerulonephritis, goodpasture's disease, crescentic glomerulonephritis, pancreatitis, dermatitis, endomyometritis, myometritis, metritis, cervicitis, endocervicitis, exocervicitis, parametritis, tuberculosis, vaginitis, vulvitis, silicosis, sarcoidosis, pneumoconiosis, inflammatory polyarthropathies, psoriatric arthropathies, intestinal fibrosis, bronchiectasis and enteropathic arthropathies.

As already stated above, the compositions of the present invention are particularly useful for treating or preventing a disease selected from chronic or acute inflammation, chronic inflammatory arthritis, rheumatoid arthritis, psoriasis, COPD, inflammatory bowel disease, septic shock, Crohn's disease, ulcerative colitis, multiple sclerosis and asthma.

Thus, in a more preferred embodiment of this invention the use of a pyrazolopyrimidine compound for the production of a pharmaceutical composition for the prophylaxis or therapy of inflammatory diseases selected from chronic or acute inflammation, chronic inflammatory arthritis, rheumatoid arthritis, psoriasis, COPD, inflammatory bowel disease, septic shock Crohn's disease, ulcerative colitis, multiple sclerosis and asthma is provided.

For the purpose of the present invention, a therapeutically effective dosage will generally be from about 1 to 500 mg/day, preferably from about 10 to about 200 mg/day, and most preferably from about 10 to about 100 mg/day, which may be administered in one or multiple doses.

It will be appreciated, however, that specific dose level of the compounds of the invention for any particular patient will depend on a variety of factors such as age, sex, body weight, general health condition, diet, individual response of the patient to be treated time of administration, severity of the disease to be treated, the activity of particular compound applied, dosage form, mode of application and concomitant medication. The therapeutically effective amount for a given situation will readily be determined by routine experimentation and is within the skills and judgment of the ordinary clinician or physician.

EXAMPLES

Example 1

Examples of Preparation of the Compounds of the Invention

General Synthetic Methods for the Compounds of the Invention, their Derivatives and Precursors In the following a general synthetic method is described.

Route AE

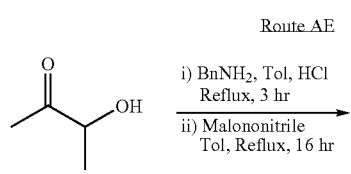

Ref: *J. Med. Chem.* 1996, 12, 2287

Pyrrole Formation

3-Hydroxy-2-butanone (1.0 eq) and benzylamine (1.0 eq) were dissolved in toluene (50 vol) and c.HCl (5 vol). The mixture was heated at 105° C., under Dean-Stark conditions, for 3 hours. The reaction was then left to stand at room temperature for 16 hours. Malonitrile was then added and the reaction heated at reflux for 16 hours. The reaction was allowed to cool to room temperature and the solvent removed in vacuo. The resultant residue was purified by column chromatography to give the desired product.

Pyrrolopyrimidone Formation

The pyrazole (1.0 eq) was dissolved in formic acid (10 vol) and the reaction heated at 110° C. for 16 hours. The reaction was allowed to cool to room temperature, diluted with water and extracted three times with ethyl acetate. The organics were combined, dried over magnesium sulfate and the solvent removed in vacuo. The resultant residue was dissolved in hot 1M KOH then neutralised with acetic acid whilst hot. The solvent was then removed in vacuo and the resultant solid taken forward to the next step without purification.

Chlorination

Pyrazolopyrimidone (1.0 eq) was dissolved in phosphorous oxychloride (18 vol), N,N-dimethylaniline (3 vol) added and the reaction heated at reflux for 5 hours. The reaction was allowed to cool, the solvent removed in vacuo and crushed ice poured onto the resultant residue. The aqueous solution was extracted with 3 portions of diethyl ether, the organics combined, dried over magnesium sulfate and the solvent removed in vacuo to give the desired product.

S$_N$Ar Reaction

The amine (1.0 eq) and the 4-Cl-pyrimidine derivative (1.0 eq) were heated at 60° C. in IPA in a sealed tube for 4-18 hours. The reaction was then allowed to cool to room temperature, and basified to pH 9-10 with 28% ammonium hydroxide solution. The resultant precipitate was isolated by filtration, washed with water, dried on the sinter, washed with diethyl ether, and dried in vacuo to give the desired product.

General Notes:
If the amine group contains an acid the reaction is not basified.
The reactions are typically carried out on a 50 mg. scale in 2-3 ml of IPA to give >10 mg product
If the reaction does not yield a precipitate, solvent is removed and the solid is triturated with water to give the desired product.

Route AF

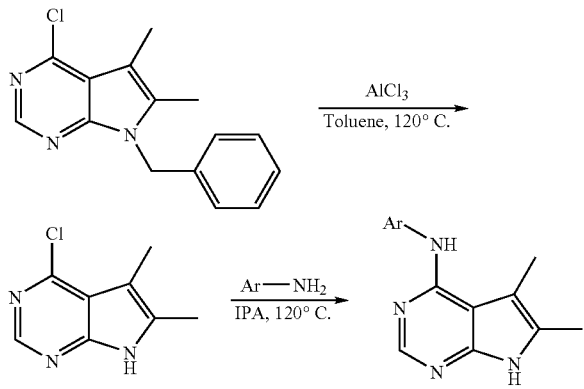

7-Benzyl-4-chloro-5,6-dimethyl-7H-pyrrolo[2,3-d]pyrimidine was prepared as for route AE.

Debenzylation

The benzylated pyrrolopyrimidine (1.0 eq) was suspended in toluene (15 vol) in a pressure tube, aluminium chloride (7 eq) added and the reaction heated at 120° C. for 4 hours. The reaction was allowed to cool and the solvent removed in vacuo. The resultant residue was then purified by column chromatography.

S$_N$Ar Reaction
As for route AE

Example 2

Kinase Fluorescence Polarization Assays

Assay principle: Inhibitory potency of compounds against Mnk1, Mnk2a and other kinases was assessed with assays based on a format known to those skilled in the art as the indirect (competitive) fluorescence polarization. The assay detection system comprises a small fluorophore-labeled phospho-peptide (termed ligand) bound to a phospho-specific antibody. The product generated by the kinase reaction competes with the ligand for antibody binding. Based on the larger molecular volume of the bound ligand, which results in a lower rotation rate in solution, its emitted light has a higher degree of polarization than the one from the free ligand.

Description of the Specific Homogenous Kinase Assay

Example 2a

Mnk1 and Mnk2a in vitro Kinase Assay

As a source of enzyme, human Mnk1 and human Mnk2a were expressed as GST fusion proteins in E. coli, purified to >80% homogeneity by glutathione affinity chromatography and activated in vitro with pre-activated ERK2. In brief, the open reading frames of human Mnk1 and Mnk2a were amplified from cDNA using the forward/reverse primer pairs

```
SEQ ID NO: 1    5'TTTAGGATCCGTATCTTCTCAAAAGTTGG/

SEQ ID NO: 2    5'CTGGGTCGACTCAGAGTGCTGTGGGCGG
and

SEQ ID NO: 3    5'ACAGGGATCCGTGCAGAAGAAACCAGCC/

SEQ ID NO: 4    5'GATGGTCGACTCAGGCGTGGTCTCCCACC
```

(utilized restriction sites underlined), respectively, and cloned into the BamHI and SalI sites of the vector pGEX-4T1 (Amersham, Sweden, cat. no. 27-4580-01). These constructs allow prokaryotic expression of Mnk1 or Mnk2a as fusion protein with a N-terminal glutathione S-transferase (GST) tag, referred to as GST-Mnk1 or GST-Mnk2a. The following expression and purification procedure was identical for GST-Mnk1 and GST-Mnk2a, referring in general to GST-Mnk, when not distinguishing between the two isoforms. Expression of GST-Mnk was in E. coli BL21 (Merck Biosciences, Germany, cat. no. 69449). Cells were grown in LB-Bouillon (Merck, Germany, cat. no. 1.10285) supplemented with 100 µg/ml ampicillin (Sigma, Germany, cat. no. A9518) at 37° C. When the culture had reached a density corresponding to an A$_{600}$ of 0.8, an equal volume of ice cold LB/ampicillin was added, the culture transferred to 25° C. and induced for 4 h with 1 mM isopropyl thiogalactoside (IPTG, Roth, Germany, cat. no. 2316.4). Cells harvested by centrifugation were resuspended in 10 ml lysis buffer (50 mM tris(hydroxymethyl)aminomethane hydrochloride (Tris/HCl, Sigma, Germany, cat. no. T5941) pH 7.5, 300 mM sodium chloride (NaCl, Sigma, Germany, cat. no. S7653), 5% (w/v) glycerol (Sigma, Germany, cat. no. G5516), 3 mM DTT dithiotreitol (DTT, Sigma, Germany, cat. no. D9779)) per gram wet weight cell pellet. Lysates were prepared by disruption of cells with a sonifier and subsequent clearing by centrifugation at 38000 g for 45 min at 4° C.

The lysate was applied to a GSTPrep FF 16/10 column (Amersham, Sweden, cat. no. 17-5234-01) equilibrated with lysis buffer. Removal of unbound material was with 3 column volumes (CV) lysis buffer. Elution was with 2 CV of elution buffer (50 mM Tris/HCl pH 7.5, 300 mM NaCl, 5% (w/v) glycerol, 20 mM glutathione (Sigma, Germany, cat. no. G4251)). Peak fractions were pooled and the protein transferred into storage buffer (50 mM Tris/HCl pH 7.5, 200 mM NaCl, 0.1 mM ethylene glycol-bis(2-aminoethylether)-N,N,N',N'-tetraacetic acid (EGTA, Aldrich, Germany, cat. no. 23,453-2), 1 mM DTT, 10% (w/v) glycerol, 0.5 M sucrose (Sigma, Germany, cat. no. S0389) by gel filtration on a PD10 desalting column (Amersham, Sweden, cat. no. 17-0851-01). Aliquots were shock frozen in liquid nitrogen and stored at −80° C.

Activation of Mnk1 and Mnk2a was at a concentration of 2.5 µM of either purified GST-Mnk1 or GST-Mnk2a by incubation with 150 nM pre-activated NHis-ERK2 (see ERK2 assay for preparation) and 50 µM adenosine triphosphate (ATP, Sigma, cat. no. A2699) in a buffer comprising 20 mM N-(2-hydroxyethyl)piperazine-N'-(2-ethanesulfonic acid) (HEPES, Fluka, Germany, cat. no 54459)/potassium hydroxide (KOH, Roth, Germany, cat. no 6751.1) pH 7.4, 10 mM magnesium chloride (MgCl$_2$, Sigma, Germany, cat. no. M2670), 0.25 mM DTT, 0.05% (w/v) polyoxyethylene 20 stearylether (Brij 78, Sigma, Germany, cat. no. P4019) (HMDB buffer) for 45 min at 30° C. After the incubation, the preparation was aliquoted into single-use samples, shock frozen in liquid nitrogen, stored at −80° C. and utilized for Mnk1 or Mnk2a kinase assays as detailed below. The presence of activating kinase has been tested to not interfere with the Mnk activity assay.

SUBSTRATE: A carboxy-terminal amidated 12 mer peptide with the sequence

SEQ ID NO: 5           TATKSG<u>S</u>TTKNR, derived from the amino acid sequence around serine 209 of the eukaryotic translation initiation factor 4E (eIF4E) has been synthesized and purified by high performance liquid chromatography (HPLC) to >95% (Thermo, Germany). The serine residue phosphorylated by Mnk kinases is underlined.

LIGAND: The peptide TATKSG-pS-TTKNR, containing an amidated carboxy-terminus and conjugated at the amino-terminus with the oxazine derived fluorophore depicted below was synthesized and used as ligand.

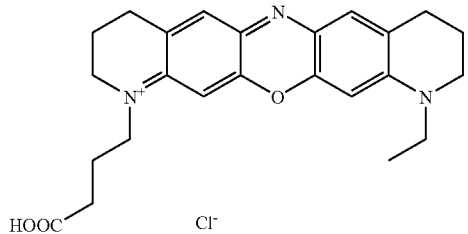 [SMILES: CCN1CCCc2cc3c(cc21)Oc1cc2c(cc1=N3)CCC[N+]=2CCCC(=O)O ; [Cl-]]

ANTIBODY: SPF New Zealand White Rabbits have been immunized according to standard protocols with the peptide NH2-CTATKSG-pS-TTKNR-CONH2, coupled to keyhole limpet hemocyanin (KLH). The immune globulin G (IgG) fraction was purified from serum of boosted animals by techniques known in the art. In brief, serum was subjected to protein A affinity chromatography. Eluted material was precipitated at 50% cold saturated ammonium sulfate, pellets dissolved and desalted. The resulting material was appropriate for use in below described assay without further antigen-specific purification.

ASSAY SETUP: Inhibition of kinase activity of Mnk1 and Mnk2a was assessed with the same assay system, using pre-activated GST-Mnk1 or GST-Mnk2a, respectively. The kinase reaction contains 30 µM substrate peptide, 20 µM ATP, 60 nM ligand and one of either 25 nM pre-activated Mnk1 or 2.5 nM pre-activated Mnk2a. The reaction buffer conditions are 16 mM HEPES/KOH pH 7.4, 8 mM $MgCl_2$, 0.4 mM DTT, 0.08% (w/v) bovine serum albumin (BSA, Sigma, Germany, cat. no. A3059), 0.008% (w/v) Pluronic F127 (Sigma, Germany, cat. no. P2443), 3% (v/v) DMSO (Applichem, Germany, cat. no. A3006). The kinase reaction is at 30° C. for 40 min. The kinase reaction is terminated by addition of 0.67 reaction volumes of 1 µM antibody in 20 mM HEPES/KOH pH 7.4, 50 mM ethylenediaminetetraacetic acid, disodium salt (EDTA, Sigma, Germany, cat. no. E5134), 0.5 mM DTT, 0.05% (w/v) polyoxyethylene-sorbitan monolaureate (Tween 20, Sigma, Germany, cat. no. P7949). After 1 h equilibration time at room temperature, samples are subjected to fluorescence polarization measurement. The fluorescence polarization readout was generated on an Analyst AD multimode reader (Molecular Devices, Sunnyvale, Calif., USA) equipped with a DLRP650 dichroic mirror (Omega Opticals, Brattleboro, Vt., USA, cat. no. XF2035), a 630AF50 band pass filter (Omega Opticals, Brattleboro, Vt., USA, cat. no. XF1069) on the excitation and a 695AF55 band pass filter on the emission side (Omega Opticals, Brattleboro, Vt., USA, cat. no. XF3076).

Example 2b

ERK2 in vitro Kinase Assay

KINASE: As a source of enzyme, human ERK2 was expressed as N-terminal hexa-histidin fusion protein in *E. coli*, purified to >80% homogeneity by immobilized metal ion affinity chromatography (IMAC) and activated in vitro with a constitutively active mutant of MEK1. In brief, the open reading frame of human ERK2 was amplified from cDNA using the forward/reverse primer pair SEQ ID NO: 6    5'AGCC<u>GTCGAC</u>GCGGCGGCGGCGGCGGCGGGC/

SEQ ID NO: 7    5'TGAC<u>AAGCTT</u>AAGATCTGTATCCTGGCTGG (utilized restriction sites underlined) and cloned into the SalI and HindIII sites of the vector pQE81L (Qiagen, Germany, cat. no. 32923). This construct allows prokaryotic expression of ERK2 as fusion protein with a N-terminal hexa-histidin tag, referred to as NHis-ERK2. Expression of NHis-ERK2 was in *E. coli* BL21. Cells were grown in LB-Bouillon supplemented with 100 µg/ml ampicillin at 37° C. When the culture had reached a density corresponding to an $A_{600}$ of 0.8, an equal volume of ice cold LB/ampicillin was added, the culture transferred to 25° C. and induced for 4 h with 1 mM IPTG. Cells harvested by centrifugation were resuspended in 10 ml lysis buffer (50 mM Tris/HCl pH 7.5, 300 mM NaCl, 5% (w/v) glycerol, 10 mM β-mercapto ethanol (Sigma, Germany, cat. no. M3148) per gram wet weight cell pellet. Lysates were prepared by disruption of cells with a sonifier and subsequent clearing by centrifugation at 38000 g for 45 min at 4° C.

The lysate was applied to a column containing 25 ml Ni-NTA Superflow matrix (Qiagen, Germany, cat. no. 1018611) equilibrated with lysis buffer. Removal of unbound material was with 3 column volumes (CV) wash buffer (50 mM Tris/HCl pH 7.5, 300 mM NaCl, 5% (w/v) glycerol, 10 mM β-mercapto ethanol, 20 mM imidazol (Sigma, Germany, cat. no. 12399)/HCl pH 7.5). Elution was with 2 CV of elution buffer (50 mM Tris/HCl pH 7.5, 300 mM NaCl, 5% (w/v) glycerol, 300 mM imidazol). Peak fractions were pooled and the protein transferred into storage buffer (50 mM Tris/HCl pH 7.5, 200 mM NaCl, 0.1 mM EGTA, 1 mM DTT, 10% (w/v) glycerol, 0.5 M sucrose) by gel filtration on a PD10 desalting column. Aliquots were shock frozen in liquid nitrogen and stored at −80° C.

The open reading frame of human MEK1 was amplified from cDNA using the forward/reverse primer pair SEQ ID NO: 8    5'GTCC<u>GGATCC</u>CCCAAGAAGAAGCCGACGCCC SEQ ID NO: 9    5'TCCC<u>GTCGAC</u>TTAGACGCCAGCAGCATGGG (utilized restriction sites underlined) and cloned into the BamHI and SalI sites of the vector pQE80L (Qiagen, Germany, cat. no. 32923). By techniques known in the art, the serine codons 212 and 214 were mutagenized to encode aspartate and glutamate. The resulting expression construct is referred to as NHis-MEK1 SSDE. This construct allows prokaryotic expression of MEK1 as a constitutively active mutant. NHis-MEK1 SSDE was expressed and purified under the conditions described for NHis-ERK2.

Activation of NHis-ERK2 was at a concentration of 11.3 µM of purified enzyme by incubation with 1 µM NHis-MEK1 SSDE and 100 µM ATP in a buffer comprising 20 mM HEPES/KOH pH 7.4, 10 mM MgCl$_2$, 0.25 mM DTT, 0.05% (w/v) Brij 78 (HMDB buffer) for 20 min at 30° C. After the incubation, the preparation was aliquoted into single-use samples, shock frozen in liquid nitrogen, stored at −80° C. and utilized for ERK2 kinase assay as detailed below and for activation of Mnk1 and Mnk2a as described above. The presence of MEK1 SSDE has been tested to not interfere with the ERK2 activity assay.

SUBSTRATE: A carboxy-terminal amidated 17 mer peptide with the sequence

SEQ ID NO: 10    FFKNIVTPR<u>T</u>PPPSQGK (synthesis by Thermo, Germany), derived from the amino acid sequence around threonine 98 of the myelin basic protein (MBP) has been synthesized and purified by HPLC to >95%. The relevant residue phosphorylated by ERK2 is underlined.

LIGAND: The peptide KNIVTPR-pT-PPPS, containing an amidated carboxy-terminus and conjugated at the amino-terminus with the fluorophore 5-carboxytetramethylrhodamine (5-TAMRA) was purchased from Thermo (Germany) and used as ligand.

ANTIBODY: Anti-phospho-MBP antibody (clone P12) was purchased from Upstate, Waltham, Mass., USA (cat. no. 05-429).

ASSAY SETUP: The kinase reaction contains 60 µM substrate peptide, 10 µM ATP and 30 nM pre-activated NHis-ERK2. The reaction buffer conditions are 16 mM HEPES/KOH pH 7.4, 8 mM MgCl$_2$, 0.4 mM DTT, 0.08% (w/v) BSA, 0.008% (w/v) Pluronic F127, 3% (v/v) DMSO.

The kinase reaction is at 30° C. for 40 min. The kinase reaction is terminated by addition of 0.67 reaction volumes of 5 nM ligand and 50 nM antibody in 20 mM HEPES/KOH pH 7.4, 50 mM EDTA, 0.5 mM DTT, 0.05% (w/v) Tween 20. After 30 min equilibration time at room temperature, samples are subjected to fluorescence polarization measurement. The fluorescence polarization readout was generated on an Analyst AD multimode reader (Molecular Devices, Sunnyvale, Calif., USA) equipped with a 561 nm dichroic mirror (Molecular Devices, Sunnyvale, Calif., USA, cat. no. 42-000-0048), a 550/10 nm band pass filter (Molecular Devices, Sunnyvale, Calif., USA, cat. no. 42-000-0130) on the excitation and a 580/10 nm band pass filter (Molecular Devices, Sunnyvale, Calif., USA , cat. no. 42-000-0034) on the emission side.

It has been shown that the particular preferred compound of the invention exhibit IC$_{50}$ values below 10 micromolar in in vitro biological screening assays for inhibition of Mnk 1 and/or Mnk 2 kinase activity.

Without being exhaustive, the following principles and methods may be employed to identify and select therapeutic compounds for use in treating inflammatory diseases and conditions as contemplated by the present invention as defined above and in the claims.

As a general principle, a system which has not been exposed to an inflammatory stimulus is exposed to such stimulus and the candidate therapeutic compound. Such system may comprise cultured cells, or components of cells, or isolated organs or tissues from animals. Alternatively, animals can be exposed to an inflammatory stimulus and the compound.

Specifically, a control group is given a known amount of inflammatory stimulus. Treatment groups are exposed to the same amount of inflammatory stimulus as well as aliquots of the candidate therapeutic compound. Inflammatory response in each group are detected by conventional means known to those of skill in the art and compared.

In particular, the following assays may be used:

Assay Utilizing Peripheral Blood Mononuclear Cells (e.g. Newton, J Leukoc Biol 39:299-311, 1986)

Human peripheral blood mononuclear cells are prepared from the peripheral blood using a ficoll-hypaque density separation (Hansell et al., J Imm Methods 145:105, 1991). Cells are cultured in appropriate medium and at appropriate density. Such density could be $10^5$ to $10^6$ cells per well of a 96-well plate. An appropriate culture medium could comprise RPMI 1640 supplemented with 10% fetal calf serum. Cells are incubated with serial dilutions of test compounds for a given time. This incubation is followed by an inflammatory stimulus applied to the cells. This stimulus could comprise LPS, or another agent, or a combination of agents. After yet another incubation, supernatant is withdrawn from the compound treated and control cells and analyzed for molecules useful for monitoring the inflammatory response. This analysis may comprise detection and quantification of cytokines (e.g., interleukins, interferones, tumor necrosis factors, chemokines), or leukotrines, or prostaglandins, or their derivatives. Detection may be with, e.g. commercially available enzyme-linked immunosorbent assays (ELISAs).

Assay for Inhibition of Cytokine Production in Lipopolysaccharide Stimulated Mice or Rats Injection of lipopolysaccharide (LPS) into mice or rats induces a rapid release of soluble cytokines into the periphery (e.g. Wichterman et al., J Surg Res 29:189-201, 1980, Beutler 1992. Tumor necrosis factors: the molecules and their emerging role in medicine. Raven Press, New York, N.Y.).

Prior to LPS injection, compounds of the invention are given either orally, or s.c., or i.v. Compounds may be given acute or sub acute. After a given time or at several given time points after LPS injection, blood is withdrawn from animals and is analysed for cytokine levels. Effects in compound treated and sham treated animals are compared.

Assay for Inhibition of Adjuvant Arthritis (Pearson, Proc Soc Exp Biol Med 91:95-101, 1956)

Adjuvant arthritis is an acute inflammatory disease induced in certain rat strains by the administration of heat-killed mycobacteria dispersed in incomplete Freund's adjuvant. The disease is manifest by severe joint swelling, mainly of the ankles and feet.

Treatment groups and control groups of rats, e.g. Lewis rats, are immunized with heat-killed mycobacteria tuberculosis emulsified in incomplete Freund's adjuvant. Thereafter, the control groups receive mock treatment, while the treatment groups receive compounds of the invention. Administration may be either orally, or s.c., or i.v. Treatment may be acute or sub acute. During the treatment phase the arthritis progression is determined by scoring the swelling of limbs.

The following animal models may be utilized as described above by the general testing principle to identify and select compounds for the indicated inflammatory diseases and conditions.

Animal Models of Inflammatory and Rheumatoid Arthritis

Animal models reflecting disease progression of inflammatory and rheumatoid arthritis have been reviewed by Brand (Comp Med 55(2):114-122, 2005). Specifically models of antigen-induced arthritis (Dumonde and Glynn, Br J Exp Pathol 43:373-383, 1962), adjuvant arthritis (Pearson, Proc Soc Exp Biol Med 91:95-101, 1956), antibody arthritis (Terato et al., J Immunol 148:2103-2108, 1992) or collagen-induced arthritis (Trentham et al., J Exp Med 146:857-868, 1977; Courtenay et al., Nature 283:666-668, 1980) may be employed to select specific compounds of the invention.

Animal Models of Inflammatory Bowel Diseases and Related Disorders

Animal models of inflammatory bowel diseases such as Crohn's disease and ulcerative colitis have been reviewed by Wirtz and Neurath (Int J Colorectal Dis 15(3):144-60, 2000). States reflecting the pathogenesis of chronic intestinal inflammation may be induced by administration of formaldehyde in combination with immune complexes (Hodgson et al., Gut 19:225-232, 1978; Mee et al., Gut 20:1-5, 1979), acetic acid (MacPherson and Pfeiffer, Digestion 17:135-150, 1978), indomethacin (Banerjee and Peters, Gut 31:1358-1364, 1990;

Yamada et al., Inflammation 17:641-662, 1993), dextran sulfate sodium (Okayasu et al., Gastroenterology 98:694-702, 1990), or haptens like trinitrobenzene sulfonic acid (TNBS)/dinitrobenzene sulfonic acid (DNBS) (Morris et al., Gastroenterology 96:795-803, 1989; Elson et al., J Immunol 157:2174-2185, 1996; Neurath et al., J Exp Med 182:1281-1290, 1995; Yamada et al., Gastroenterology 102:1524-1534, 1992; Dohi et al., J Exp Med 189: 1169-1180, 1999) or oxazolone (Ekstrom, Scand J Gastroenterol 33:174-179, 1998; Boirivant et al., J Exp Med 188:1929-1939,1998).

Animal Models of Septic Shock

Animal models of septic shock expose specimen to lipopolysaccharide (LPS), gram-negative or gram-positive bacteria, or combinations thereof (Wichtermanet al., J Surg Res 29:189-201, 1980; Fink and Heard, J Surg Res 49(2):186-96, 1990). The rodent model of cecal ligation and puncture (CLP) resembles the situation of bowel perforation and mixed bacterial infection of intestinal origin (Baker et al., Surgery 94:331-335, 1983).

Animal Model of Psoriasis

To invest the suitability of compounds for the treatment of psoriasis, the human psoriatic skin xenotransplantation model (Nickoloff, Arch Dermatol 135:1104-1110, 1999; Nickoloff, J Invest Dermatol Symp Proc 5:67-73, 2000) may be utilized.

Animal Model of Allergic Asthma

In a commonly employed rodent model of allergic asthma animals are sensitized to an antigen (e.g. ovalbumin) and are subsequently challenged with the same antigen by inhalation of an aerosol (e.g. Fujitani et al., Am J Respir Crit Care Med 155:1890-1894, 1997; Kanehiro et al., Am J Respir Crit Care Med 163:173-184, 2001; Henderson et al., Am J Respir Crit Care Med 165:108-116, 2002; Oh et al., J Immunol 168: 1992-2000, 2002).

The invention claimed is:

1. A compound of the general formula (1)

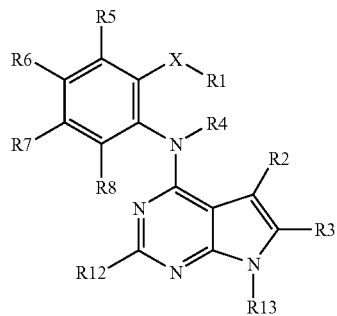

wherein X is O;

$R_1$ is hydrogen, $C_{1-6}$alkyl, $C_{1-6}$ alkyl $C_{3-10}$ cycloalkyl, $C_{3-10}$ cycloalkyl, $C_{1-6}$ alkyl 3 to 10 membered heterocyclyl comprising at least one heteroatom selected from N, S and O, 3 to 10 membered heterocyclyl comprising at least one heteroatom selected from N, S and O, $C_{6-10}$ aryl, $C_{1-6}$ alkyl $C_{6-10}$ aryl, $C_{5-10}$ heteroaryl comprising at least one heteroatom selected from N, S and O, or $C_{1-6}$ alkyl $C_{5-10}$ heteroaryl comprising at least one heteroatom selected from N, S and O, wherein $R_1$ is optionally substituted with one or more $R_9$;

$R_2$ and $R_3$ are the same or different and are independently selected from hydrogen and $C_{1-6}$ alkyl;

$R_4$ is hydrogen, $C_{1-4}$ alkyl, urea, thiourea or acetyl optionally substituted with one or more $R_9$;

$R_5$, $R_6$, $R_7$ and $R_8$ are the same or different and are independently selected from H or $R_9$;

$R_9$ is independently halogen; CN; COOR$_{11}$; OR$_{11}$; C(O)N(R$_{11}$R$_{11a}$); S(O)$_2$N(R$_{11}$R$_{11a}$); S(O)N(R$_{11}$R$_{11a}$); S(O)$_2$R$_{11}$; N(R$_{11}$)S(O)$_2$N(R$_{11a}$R$_{11b}$); SR$_{11}$; N(R$_{11}$R$_{11a}$); OC(O)R$_{11}$; N(R$_{11}$)C(O)R$_{11a}$; N(R$_{11}$)S(O)$_2$R$_{11a}$; N(R$_{11}$)S(O)R$_{11a}$; N(R$_{11}$)C(O)N(R$_{11a}$R$_{11b}$); N(R$_{11}$)C(O)OR$_{11a}$; OC(O)N(R$_{11}$R$_{11a}$); oxo (=O), where the ring is at least partially saturated; C(O)R$_{11}$; C$_{1-6}$ alkyl; phenyl; C$_{3-7}$ cycloalkyl; or heterocyclyl, wherein C$_{1-6}$ alkyl; phenyl; C$_{3-7}$ cycloalkyl; and heterocyclyl are optionally substituted with one or more R$_{10}$;

$R_{10}$ is independently halogen; CN; OR$_{11}$; S(O)$_2$N(R$_{11}$R$_{11a}$); S(O)N(R$_{11}$R$_{11a}$); S(O)$_2$R$_{11}$; N(R$_{11}$)S(O)$_2$N(R$_{11a}$R$_{11b}$); SR$_{11}$; N(R$_{11}$R$_{11a}$); OC(O)R$_{11}$; N(R$_{11}$)C(O)R$_{11a}$; N(R$_{11}$)S(O)$_2$R$_{11a}$; N(R$_{11}$)S(O)R$_{11a}$; N(R$_{11}$)C(O)N(R$_{11a}$R$_{11b}$); N(R$_{11}$)C(O)OR$_{11a}$; OC(O)N(R$_{11}$R$_{11a}$); oxo (=O), where the ring is at least partially saturated; C(O)R$_{11}$; C$_{1-6}$ alkyl; phenyl; C$_{3-7}$ cycloalkyl; or heterocyclyl, wherein C$_{1-6}$ alkyl; phenyl; C$_{3-7}$ cycloalkyl; and heterocyclyl are optionally substituted with one or more R$_9$;

$R_{11}$, $R_{11a}$, $R_{11b}$ are independently selected from the group consisting of hydrogen, C$_{1-6}$ alkyl, C$_{1-6}$ alkyl C$_{3-10}$ cycloalkyl, C$_{3-10}$ cycloalkyl, C$_{1-6}$ alkyl 3 to 10 membered heterocycloalkyl comprising at least one heteroatom selected from N, S and O, 3 to 10 membered heterocycloalkyl comprising at least one heteroatom selected from N, S and O, C$_{6-10}$ aryl, 5 to 10 membered heteroaryl comprising at least one heteroatom selected from N, S and O, wherein R$_{11}$, R$_{11a}$, R$_{11b}$ are optionally substituted with one or more R$_9$;

$R_{12}$ is hydrogen;

$R_{13}$ is hydrogen, C$_{1-6}$ alkyl, C$_{1-6}$ alkyoxycarbonyl, C$_{6-10}$ aryloxycarbonyl, C$_{6-10}$ aralkoxycarbonyl, carbamoyl or acyl;

or a pharmaceutically acceptable salt thereof.

2. The compound according to claim 1 wherein
$R_2$ and $R_3$ are the same or different and are independently selected from hydrogen, methyl, ethyl and propyl;
$R_4$ is hydrogen or C$_{1-4}$ alkyl;
$R_5$, $R_6$, $R_7$ and $R_8$ are the same or different and are independently selected from hydrogen, CONH$_2$, CO$_2$H, CO$_2$CH$_3$, Cl and F;
or a pharmaceutically acceptable salt thereof.

3. The compound according to claim 1, wherein
$R_1$ is hydrogen, methyl, ethyl, propyl, butyl, difluoromethyl, bromoethyl, 1,1,2,2-tetrafluoroethyl, 1,1,1-trifluoropropyl, perfluoromethyl, cyclopropylmethyl, cyclopentyl, cyclohexyl, adamantyl, norbonanyl, tetrahydrofuranyl, tetrahydropyranyl, phenyl or pyrrolidin-3-yl substituted at the nitrogen with R$_9$;
$R_2$ and $R_3$ are the same or different and are independently selected from hydrogen, methyl, ethyl and propyl;
$R_4$ is hydrogen or C$_{1-4}$ alkyl;
$R_5$, $R_6$, $R_7$ and $R_8$ are the same or different and are independently selected from hydrogen, CONH$_2$, CO$_2$H, CO$_2$CH$_3$, Cl and F;
or a pharmaceutically acceptable salt thereof.

4. The compound according to claim 1, wherein
$R_2$ and $R_3$ are the same or different and are selected from methyl and hydrogen.

5. The compound according to claim 1, wherein
$R_1$ is hydrogen, C$_{1-6}$ alkyl, C$_{1-6}$ alkyl C$_{3-10}$ cycloalkyl, C$_{3-10}$ cycloalkyl, 5 to 10 membered heterocyclyl comprising at least one heteroatom selected from N, S and O, C$_{6-10}$ aryl, C$_{1-6}$ alkyl C$_{6-10}$ aryl, C$_{5-10}$ heteroaryl comprising at least one heteroatom selected from N, S and O, C$_{1-6}$ alkyl C$_{5-10}$ heteroaryl comprising at least one heteroatom selected from N, S and O, wherein R$_1$ is optionally substituted with one or more R$_9$;

$R_2$ and $R_3$ are the same or different and are independently selected from hydrogen and C$_{1-4}$ alkyl;
$R_4$ is hydrogen or C$_{1-4}$ alkyl;
$R_5$, $R_6$, $R_7$ and $R_8$ are the same or different and are independently selected from hydrogen, CO$_2$H, CO$_2$R$_{1c}$, CONH$_2$, CONHR$_{1d}$ and halogen, whereby R$_{1c}$ and R$_{1d}$ are C$_{1-6}$ alkyl;
or a pharmaceutically acceptable salt thereof.

6. The compound according to claim 1, wherein R$_4$ is hydrogen.

7. The compound according to claim 1, wherein each cycloalkyl group is adamantyl or norbonanyl, cyclohexyl or cyclopentyl.

8. The compound according to claim 1, wherein each halogen atom is selected from Cl, Br and F.

9. The compound according to claim 1, wherein R$_5$, R$_6$, R$_7$ and R$_8$ are hydrogen.

10. The compound according to claim 1, wherein at least one of R$_5$, R$_6$, R$_7$ and R$_8$ is F, CONH$_2$ or CO$_2$CH$_3$.

11. The compound according to claim 4, wherein R$_1$ is hydrogen, methyl, ethyl, propyl, butyl, difluoromethyl, bromoethyl, 1,1,2,2-tertrafluoroethyl, 1,1,1trifluoropropyl, perfluoromethyl, cyclopropylmethyl, cyclopentyl, cyclohexyl, adamantyl, norbonanyl, tetrahydrofuranyl, tetrahydropyranyl, phenyl or pyrrolidin-3-yl substituted at the nitrogen with R$_9$, wherein R$_9$ is as defined in claim 1.

12. The compound according to claim 1, wherein R$_4$, R$_7$ and R$_8$ are hydrogen.

13. The compound according to claim 1, wherein R$_6$ is C(O)NH$_2$.

14. The compound according to claim 1, wherein R$_6$ is C(O)NH$_2$ and R$_1$ is selected from C$_{3-7}$ cycloalkyl, C$_{1-6}$ alkyl and a 3 to 10 membered heterocyclyl group comprising at least one heteroatom selected from N, S and O.

15. The compound according to claim 1 selected from the group consisting of:

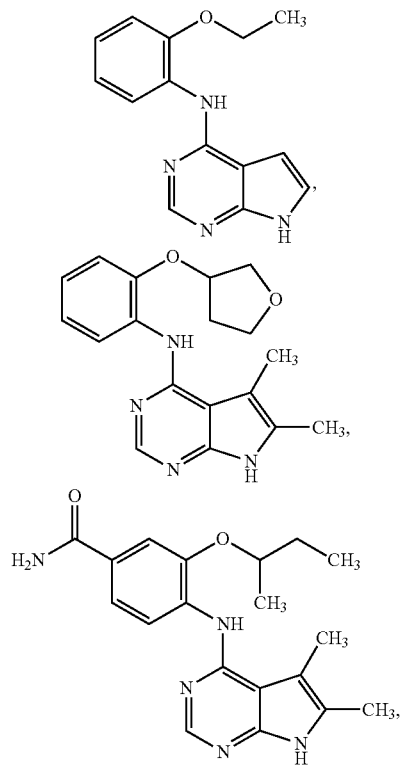

-continued
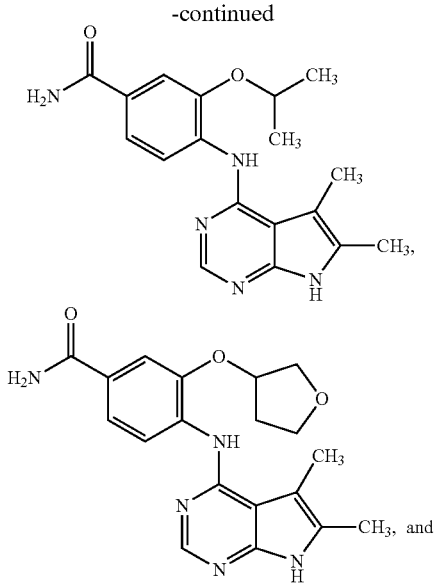
-continued
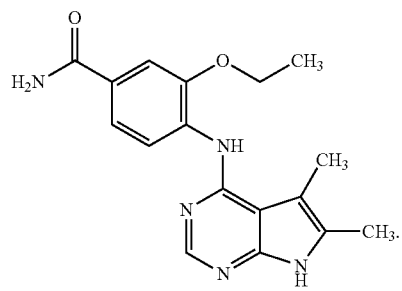
16. A pharmaceutical composition comprising a compound according to claim 1 and optionally a pharmaceutically acceptable carrier.
* * * * *

UNITED STATES PATENT AND TRADEMARK OFFICE
CERTIFICATE OF CORRECTION

| | | |
|---|---|---|
| PATENT NO. | : 8,697,713 B2 | Page 1 of 1 |
| APPLICATION NO. | : 12/373224 | |
| DATED | : April 15, 2014 | |
| INVENTOR(S) | : Stefan Jäkel et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 771 days.

Signed and Sealed this
Twenty-fourth Day of November, 2015

Michelle K. Lee
*Director of the United States Patent and Trademark Office*